US005808005A

United States Patent [19]
Codington et al.

[11] Patent Number: 5,808,005
[45] Date of Patent: Sep. 15, 1998

[54] HUMAN CARCINOMA ANTIGEN

[75] Inventors: John F. Codington, W. Newton, Mass.; Svein Haavik, Drobak, Norway

[73] Assignee: Epigen, Inc., Millbrook, N.Y.

[21] Appl. No.: 484,061

[22] Filed: Jun. 6, 1995

Related U.S. Application Data

[60] Division of Ser. No. 192,840, Feb. 7, 1994, Pat. No. 5,545,532, which is a continuation-in-part of Ser. No. 14,450, Feb. 5, 1993, abandoned.

[51] Int. Cl.$^6$ .................................................. C07K 14/705
[52] U.S. Cl. .................. 530/395; 530/387.2; 530/277.1; 436/813; 436/64; 435/7.23
[58] Field of Search .......................... 435/7.23; 436/813, 436/64; 530/387.2, 395; 424/277.1

[56] References Cited

U.S. PATENT DOCUMENTS

| | | |
|---|---|---|
| Re. 32,417 | 5/1987 | Burchiel et al. ........................... 424/1.1 |
| 3,867,363 | 2/1975 | Hansen ...................................... 424/12 |
| 3,956,258 | 5/1976 | Hansen ...................................... 424/88 |
| 3,967,638 | 7/1976 | Tondreau . |
| 4,086,217 | 4/1978 | Hansen . |
| 4,180,499 | 12/1979 | Hansen . |
| 4,628,032 | 12/1986 | White et al. . |
| 4,708,930 | 11/1987 | Kortright et al. . |
| 4,713,352 | 12/1987 | Bander et al. ........................... 436/548 |
| 4,732,862 | 3/1988 | Bartorelli ................................ 436/513 |
| 4,743,543 | 5/1988 | Kortright . |
| 4,837,171 | 6/1989 | Codington ............................... 436/548 |
| 4,888,275 | 12/1989 | Holmgren et al. . |
| 4,892,934 | 1/1990 | Yoshida et al. . |
| 4,892,935 | 1/1990 | Yoshida et al. . |
| 4,914,021 | 4/1990 | Toth et al. . |
| 4,918,164 | 4/1990 | Hellstom et al. . |
| 4,921,789 | 5/1990 | Salem et al. . |
| 4,921,790 | 5/1990 | O'Brien . |
| 4,939,240 | 7/1990 | Chu et al. ............................ 530/387.1 |
| 4,963,484 | 10/1990 | Kufe . |
| 5,019,497 | 5/1991 | Olsson . |
| 5,030,621 | 7/1991 | Bystryn ..................................... 514/21 |
| 5,053,489 | 10/1991 | Kufe . |
| 5,110,911 | 5/1992 | Samuel et al. . |
| 5,118,611 | 6/1992 | Smith et al. . |

FOREIGN PATENT DOCUMENTS

| | | |
|---|---|---|
| 394510 | 4/1989 | European Pat. Off. . |
| 370768 | 11/1989 | European Pat. Off. . |
| WO89/07268 | 8/1989 | WIPO . |
| WO 90/14433 | 1/1990 | WIPO . |
| WO90/02333 | 3/1990 | WIPO . |
| WO90/05540 | 5/1990 | WIPO . |
| WO90/06773 | 6/1990 | WIPO . |
| WO90/12320 | 10/1990 | WIPO . |

OTHER PUBLICATIONS

Barak, M., et al., "CA–15.3, TPA and MCA as Markers for Breast Cancer", 1990, *Eur. J. Cancer*, vol. 26, pp. 577–580.
Becker, S.N., et al., "Scanning Electron Microscopy of Alcohol–Fixed Cytopathology Specimens", 1981, *Acta Cytologica*, vol. 25, pp. 578–584.

Bhavanadan, V.P., "Malignancy–related Cell Surface Mucin–Type Glycoproteins", 1988, *Indian J. of Biochem. & Biophys.*, vol. 25, pp. 36–42.
Carraway, K.L., et al., "Structural and Functional Aspects of Tumor Cell Sialomucins", 1986, *Molecular and Cell. Biochem.*, vol. 72, pp. 109–120.
Clausen, H., et al., "ABH and Related Histo–Blood Group Antigens; Immunochemical Differences in Carrier Isotypes and Their Distribution", 1989, *Vox Sanguinis, Int'l J. Transfusions*, vol. 56, pp. 1–20.
Clausen, H., et al., "Monoclonal Antibodies Directed to the Blood Group A Associated Structure, Galactosyl–A: Specificity and Relation to the Thomsen–Friedenreich Antigen", 1988, *Molec. Immunol.*, vol. 25, pp. 199–204.
Codington, J.F., et al., "Glycoprotein Coat of the TA3 Cell. Isolation and Partial Characterization of a Sialic Acid Containing Glycoprotein Fraction", 1972, *Biochemistry*, vol. 11, pp. 2559–2564.
Codington, J.F., et al., "Epiglycanin–A Carcinoma–Specific Mucin–Type Glycoprotein of the Mouse TA3 Tumour", 1992, *Glycobiology*, vol. 2, pp. 173–180.
Codington, J.F., et al., "Antibody to Epiglycanin and Radioimmunoassay to Detect Epiglycanin–Related Glycoproteins in Body Fluids of Cancer Patients", 1984, *J. Nat'l. Cancer Inst.*, vol. 73, pp. 1029–1038.
Codington, J.F., et al., "Isolation and Partial Characterization of an Epiglycanin–Like Glycoprotein From a New Non–Strain–Specific Subline of TA3 Murine Mammary Adenocarcinoma", 1979, *J. Nat'l. Cancer Inst.*, vol. 63 pp. 153–160.
Codington, J.F., et al., "Evidence that the Major Cell Surface Glycoprotein of the TA3–Ha Carcinoma Contains the Vicia Graminea Receptor", 1975, *Biochemistry*, vol. 14, pp. 855–859.

(List continued on next page.)

*Primary Examiner*—Toni R. Scheiner
*Attorney, Agent, or Firm*—Hamilton, Brook, Smith & Reynolds, P.C.

[57] ABSTRACT

A glycoprotein antigen which is generally characteristic of human carcinomas, regardless of the tissue associated with the carcinoma—human carcinoma antigen (HCA)—and which is generally not present on normal human cells. Immunodeterminant-containing fragments of HCA substantially separated from elements of HCA's naturally occurring environment are also disclosed. HCA is generally characterized by: a) a molecular weight in excess of 750,000; b) carbohydrate moieties characteristic of mucin-type glycoproteins and comprising a relatively high proportion of sialic acid, galactose, and N-acetylgalactosamine residues (e.g., at least 50% of the carbohydrate residues are sialic acid, galactose, or N-acetylgalactosamine residues); c) an isoelectric point below pH 3.0; d) presence generally on human carcinoma cells; e) absence generally from non-transformed human cells; f) at least one immunodeterminant that specifically reacts with anti-murine epiglycanin antibody AE3; and g) general insolubility in aqueous fluids (e.g., a phosphoric acid or an HCl solution) below pH 2.0 Also disclosed are antibodies to HCA, immunoassays for HCA, in vivo imaging using HCA-binding antibodies and therapeutics using HCA or anti-idiotypic HCA antibodies.

13 Claims, 21 Drawing Sheets

OTHER PUBLICATIONS

Codington, J.F., et al., "Cell–Surface Glycoproteins of Two Sublines of the TA3 Tumor", 1973, *J. Nat'l. Cancer Institute*, vol. 51, pp. 585–591.

Dodd, J., et al., The Value of the Monoclonal Antibody (Cancer Antigen 125) in Serial Monitoring of Ovarian Cancer: a Comparison with Circulating Immune Complexes, 1985, *Brit. J. Obstetrics and Gynaecology*, vol. 92, pp. 1054–1060.

Haavik, S., et al., "Development and Characterization of Monoclonal Antibodies Against a Mucin–Type Glycoprotein", 1992, *Glycobiology*, vol. 2, pp. 217–224.

Hanisch, F.G., et al., "Structural Studies on Oncofetal Carbohydrate Antigens (CA 19–9, CA 50, and CA 125) Carried By O–Linked Sialyloligosaccharides on Human Amniotic Mucins", 1988, *Carbohydr. Res.*, vol. 178, pp. 29–47.

Henningsson, C.M., et al., "T Cell Recognition of a Tumor–Associated Glycoprotein and its Synthetic Carbohydrate Epitopes: Stimulation of Anticancer T Cell Immunity In Vivo", 1987, *Cancer Immunol. Immunother*, vol. 25, pp. 231–241.

Hilkens, J., "Biochemistry and Function of Mucins in Malignant Disease", 1988, *Cancer Rev.*, vol. 11–12, pp. 25–54.

Hinoda, Y., "Immunochemical Characterization of Adenocarcinoma–Associated Antigen YH206", *Int'l. J. Cancer*, vol. 42, pp. 653–658.

Ishida, M., et al., "Related Glycoproteins from Normal Secretory and Malignant Breast Cells", 1989, *Tumor Biol.*, vol. 10, pp. 12–22.

Kjeldsen, et al., "Preparation and Characterization of Monoclonal Antibodies Directed to the Tumor–Associated O–linked Sialosyl-2→6 α–N–Acetylgalactosaminyl (Sialosyl–Tn) Epitope", 1988, *Cancer Research*, vol. 48, pp. 2214–2220.

Laemmli, U.K., "Cleavage of Structural Proteins During the Assembly of the Head of Bacteriophage T4", 1970, vol. 227, pp. 680–685.

Lan, M.S., et al., "Cloning and Sequencing of a Human Pancreatic Tumor Mucin cDNA", 1990, *J. Biological Chem.*, vol. 265, pp. 15294–15299.

Lan, M.S., et al., "Isolation and Properties of a Human Pancreatic Adenocarcinoma–associated Antigen, DU–PAN–2", 1985, vol. 45, pp. 305–310.

Leiter, J., et al., "Cancer Chemotherapy Screening Data XXXIII", *Cancer Research Supp.*, vol. 25, pp. 11–12.

Marsella, R.C., et al., "Identification of Adenocarcinoma in Effusions: A Comparison of Immunoperoxidase Staining for Monoclonal Antibody B72.3 and Carcinoembryonic Antigen", *Acta Cytologica*, vol. 34, pp. 578–580.

Marx, J.L., "Cancer Vaccines Show Promise at Last", *Science Res. News*, vol. 245, pp. 813–815.

Richardson, G., "KLE: A Cell Line with Defective Estrogen Receptor Derived From Undifferentiated Endometrial Cancer", 1984, *Gynecologic Oncology*, vol. 17, pp. 213–230.

Sheer, D.G., et al., "Purification and Composition of the Human Tumor–associated Glycoprotein (TAG–72) Defined by Monoclonal Antibodies CC49 and B72.3", 1988, *Cancer Research*, vol. 48, pp. 6811–6818.

Slayter, H.S., et al., "Configuration of Glycoprotein Fragments Cleaved from Tumor Cells by Proteolysis", 1973, *J. Biological Chem.*, No. 10, pp. 3405–3410.

Spicer, A.P., et al., "Molecular Cloning and Analysis of the Mouse Homologue of the Tumor–Associated Mucin, MUC1, Reveals Conservation of Potential O–Glycosylation Sites, Transmembrane, and Cytoplasmic Domains and a Loss of Minisatellite–like Polymorphism", 1991, *J. Biological Chem.*, vol. 266, pp. 15099–15109.

Springer, G.F., et al., "Blood Group Tn–Active Macromolecules from Human Carcinomas and Erythrocytes: Characterization of and Specific Reactivity with Mono–and Polyclonal Anti–Tn Antibodies Induced by Various Immunogens", 1988, *Carbohydrate Research*, vol. 178, pp. 271–292.

Tjandra, J.J., et al., "Application of Mammary Serum Antigen Assay in the Management of Breast Cancer: A Preliminary Report", 1988, *British J. Surg.*, vol. 75, pp. 811–817.

Van den Eijnden, et al., "Chemical Structure of Epiglycanin, the Major Glycoprotein of the TA3–Ha Ascites Cell", 1979, *J. Biological Chem.*, vol. 254, pp. 12153–12159.

Watkins, S.C., et al., "Intracellular Pathway of a Mucin–Type Membrane Glycoprotein in Mouse Mammary Tumor Cells", 1991, vol. 213, pp. 185–200.

Weitzhandler, M., et al., "Monosaccharide and Oligosaccharide Analysis of Proteins Transferred to Polyvinylidene Fluoride Membranes after Sodium Dodecyl Sulfate–Polyacrylamide Gel Electrophoresis", *J. Biolog. Chem.*, vol. 268, pp. 5121–5130.

PVDF BLOT OF SDS-PAGE (8%)
HC-antigen from the KLE cell line

HUMAN CARCINOMA ANTIGEN

This is a divisional of application Ser. No. 08/192,840, filed Feb. 7, 1994, now U.S. Pat. No. 5,545,532 which is a continuation-in-part of application Ser. No. 08/014,450, filed Feb. 5, 1993, which is now abandoned.

BACKGROUND OF THE INVENTION

This invention relates to antigen markers characteristic of tumors, antibodies to those markers, and immunoassays based on those markers. It also relates to vaccines and to tumor imaging and immunotherapy using tumor specific reagents.

When exposed to foreign substances, the immune system produces proteins, known as antibodies, which specifically bind to those foreign substances. The substances which trigger antibody production, and to which antibodies bind, are known as antigens.

Antigens present on the surface of cells may serve as cell-surface markers, and the presence of such markers can be detected by antibodies that are specific for them. In that way antibodies are used to detect the presence of cells. Since cells can be characterized by the markers they possess, it is possible to identify cell types using antibodies.

Many cell surface markers are glycosylated proteins (glycoproteins). Notable among the glycoproteins are mucin-type glycoproteins, which are large molecules with a high proportion of carbohydrate chains that are O-linked through N-acetylgalactosamine to serine and/or threonine in the protein core.

There are various reports of antigens, some of which are mucin-type glycoproteins, that appear on the surfaces of tumor cells but not on the surfaces of normal cells of the same host. There are also various disclosures related to the use of such tumor specific antigens and antibodies to these antigens.

For example, there is a significant body of literature reporting studies on a sialomucin known as epiglycanin, which is found at the surface of the mouse carcinoma cell line TA3-Ha. Epiglycanin was first reported in 1972 by Codington et al., (1972) *Biochemistry* 11:2559–2564. Mild proteolysis of viable TA3-Ha ascites cells with TPCK-trypsin, followed by fractionation of the released peptides by gel exclusion chromatography, gave a peak of glycopeptide material of high molecular weight, and that material has been the subject of numerous subsequent studies: Codington et al., (1973) *J. Nat'l Cancer Inst.* 51:585–591; Slayter et al., (1973) *J. Biol. Chem.* 248:3405–3410; Codington et al., (1975) *Biochemistry* 14:855–859; Codington et al., (1979) *J. Nat'l Cancer Instit.* 63:153–162; Watkins et al., (1990) *Carbohydr. Res.* 213:185–200; Henningson et al., (1987) *Cancer Immunol. Immunother.* 25:231–241. Epiglycanin is generally characterized as having a molecular weight of 500,000, about 80% of which is carbohydrate, largely GalB (1→3) GalNAc side chains linked to serine or threonine residues in a polypeptide chain of about 1,300 amino acids. See, Van den Eijnden et al., (1979) *J. Biol. Chem.* 254:12153–12159. For reviews of this literature, see Codington et al., (1992) *Glycobiology* 2:173–180; and Haavik et al., (1992) *Glycobiology* 2:217–224.

Polyclonal antibodies to epiglycanin have been reported in Codington et al., (1984) *J. Nat'l Cancer Instit.* 73:1029–1038. Several monoclonal antibodies to epiglycanin have also been reported. Codington, U.S. Pat. No. 4,837,171; Haavik et al., (1992) *Glycobiology* 2(3): 217–224. The polyclonal antibodies were found to react with a substance in peritoneal or pleural fluid and in sera of patients with metastatic cancer. Codington et al., (1984) *J. Nat'l Cancer Inst.* 73:1029–1038.

Other tumor specific markers have been reported.

Samuel et al., in U.S. Pat. No. 5,110,911, report an adenocarcinoma-derived antigen which is shed by human tumor cells. This glycoprotein, termed Thomsen-Friedenreich (TF) antigen, has a molecular weight greater than 1,000,000 and is characterized by a non-cryptic Galβ (1→3)GalNAc epitope.

Kortright, in U.S. Pat. Nos. 4,708,930 and 4,743,543, reports a murine monoclonal antibody specific for an antigenic determinant on the surface or in the cytoplasm of human carcinoma cells and tissue. The antigenic determinant is designated "KC-4 antigen" and is said to appear in two forms, one having a molecular weight of 480,000–510,000 and the second having a molecular weight of 390,000–450,000. The KC-4 antigen was developed from human prostate adenocarcinoma.

Salem et al., in U.S. Pat. No. 4,921,789 report an antigen marker for human colorectal cancer, having a molecular weight of about 160,000. The antigen is said to be non-reactive with antibodies to certain other antigens.

O'Brien, in U.S. Pat. No. 4,921,790, reports a subunit of CA125 antigen, an antigen associated with cystadenocarcinoma of the ovary. The CA125 antigen has a molecular weight of about 40,000.

Kufe, in U.S. Pat. Nos. 4,963,484 and 5,053,489, reports identification (by recombinant methods) of a peptide determinant of the DF3 antigen from human breast carcinoma.

Chu et al., in U.S. Pat. No. 4,939,240, report a monoclonal antibody said to reduce the mass of a human breast tumor xenograft in a mouse.

Hellstrom et al., in U.S. Pat. No. 4,918,164, report a monoclonal anti-idiotypic antibody having an antigen combining site related to that of the p97 antigen of human melanoma.

Toth et al., in U.S. Pat. No. 4,914,021, report a monoclonal antibody specific for an antigen termed carcinoma or orosomucoid-related antigen (CORA). CORA is said to have a molecular weight of about 46,000–50,000, an isoelectric point of 3.0–3.5, and a carbohydrate content of 30% (by weight).

Yoshida, in U.S. Pat. No. 4,892,935, report an antibody to a human pulmonary carcinoma antigen which reacts with human squamous cell lung carcinoma but not with human small cell lung carcinoma.

Kjeldsen et al., (1988) *Cancer Res.* 48:2214–2220, report a breast carcinoma glycoprotein termed TAG-72.

Springer et al., (1988) *Carbohydr. Res.* 178:271–292, report T and Tn haptens in glycoproteins of human breast carcinoma.

Tjandra et al., (1988) *Br. J. Surg.* 75:811–817, report a breast carcinoma glycoprotein termed MSA.

Ishida et al., (1989) *Tumor Biol.* 10:12–22, report a breast carcinoma antigen termed MFGM.

Lan et al., (1985) *Cancer Res.* 45:305–310, report a pancreatic carcinoma antigen termed DU-PAN-2.

Hanisch et al., (1988) *Carbohydr. Res.* 178:29–47, report an ovarian carcinoma antigen termed CA125.

Hinoda et al., (1988) *Cancer J.* 42:653–658, report a lung carcinoma antigen termed YH206.

SUMMARY OF THE INVENTION

We have discovered a glycoprotein antigen which is generally characteristic of human carcinomas, regardless of the epithelial tissue of origin. We call this antigen human carcinoma antigen (HCA). HCA is generally not present on normal human cells. One aspect of the invention, in its broadest form, features HCA and immunodeterminant-containing fragments of HCA substantially separated from elements of HCA's natural environment. By immunodeterminants, we mean portions of HCA which are sufficient to bind to a monospecific anti-HCA monoclonal antibody or that are sufficient (alone or as a hapten conjugate) to raise an HCA-specific immune response in a mammal. We have found that HCA fragments having a molecular weight under about 50,000 generally do not present suitable immunodeterminants. A substance is substantially separated from elements of HCA's naturally occurring environment when it is sufficiently purified or isolated to be used in the various methods of the invention discussed below, for example, to be used as an immunogen to raise anti-HCA antibodies or as a competitive antigen in a competitive immunoassay. For example, the HCA in a washed immunocomplex of HCA and HCA-binding antibody (such as would be produced in performing an immunoassay (competitive or ELISA) that uses a non-radioactive label) may be considered as substantially separated from HCA's natural environment.

HCA is generally characterized by:
a) a molecular weight in excess of 750,000;
b) carbohydrate moieties characteristic of mucin-type glycoproteins and comprising a relatively high proportion of sialic acid, galactose, and N-acetylgalactosamine residues (i.e., the sum of the weight of those three residues makes up a high proportion (e.g., at least 60%) by weight of total carbohydrate content);
c) an isoelectric point below pH 3.0;
d) presence generally on human carcinoma cells;
e) absence generally from non-transformed human cells;
f) at least one immunodeterminant that specifically reacts with anti-murine epiglycanin antibody AE3 (produced by hybridoma HAE-3, deposited in accordance with the provisions of the Budapest Treaty at the American Tissue Type Culture Collection (ATCC), Rockville, Md. 20852, on Jul. 1, 1987, and assigned ATCC accession no. HB-9467); and
g) general insolubility in aqueous fluids (e.g., a phosphoric acid or an HCl solution) below pH 2.0;

More typically, HCA has a molecular weight over 1 million and an isoelectric point less than pH 2.5. HCA is generally found on tumor cells, for example on cells from colon, lung, pancreatic, mammary, prostate, and ovarian tumors of epithelial origin.

HCA may be generally characterized by affinity for anti-mouse epiglycanin antibodies. Affinity for some such antibodies may be dependent on the presence of an immunodeterminant that is sensitive to (i.e., immunoreactivity is substantially reduced or destroyed by) O-glycanase, periodate, or both, and affinity for some such antibodies may be enhanced by desialylation of HCA. HCA is also characterized by the presence of at least 50% by weight carbohydrate.

HCA may also be characterized based on monosaccharide composition. HCA comprises fucose, N-acetylgalactosamine, N-acetylglucosamine, galactose, mannose, and N-acetyl neuraminic acid, preferably in the following amounts (±10%–40%), as determined by hydrolysis of HCA using trifluoroacetic acid, followed by determination of monosaccharide composition by HPAEC-PAD: fucose, 3.6%; N-acetylgalactosamine, 15.2%; N-acetylglucosamine, 11.2%; galactose, 27.8%; mannose, 25.6%; N-acetyl neuraminic acid, 16.6%.

Amino acid composition may also be used to characterize HCA. HCA comprises each of the following amino acid residues: Serine, Threonine, Glutamine, Asparagine, Leucine, Alanine, Glycine, Valine, Proline, Lysine, Isoleucine, Arginine, Phenylalanine, Tyrosine, Histidine, Cysteine. Each amino acid, Proline, Phenylalanine, Tyrosine or Cysteine, comprises 0–5% of the total amino acid residues of HCA. Preferably, the amino acids are present in the following amounts (±20%) as determined by hydrolysis of HCA using 6M HCl in vacuo, followed by amino acid analysis: Serine, 10.2%; Threonine, 3.6%; Glutamine, 14.6%; Asparagine, 8.2%; Leucine, 14.5%; Alanine, 6.6%; Glycine, 23.4%; Valine, 3.7%; Proline, <1.0%; Lysine, 4.8%; Isoleucine, 3.7%; Arginine, 4.3%; Phenylalanine, <1.0%; Tyrosine, <1.0%; Histidine, 2.4%; Cysteine, <1.0%;

HCA is also characterized by a buoyant density of 1.3–1.45 g/ml, preferably 1.34–1.41 g/ml, as determined by centrifugation in 47% cesium trifluoroacetate in accordance with the procedure described in Example 19. Ability to bind to epiglycanin-specific antibodies, e.g., AE3, AD7, and BF11, can also be used to characterize HCA. HCA may be characterized by the ability to bind to antibody AE3 with an affinity that is at least 100× the affinity for antibody 49H.8.

Our discovery of HCA enables other aspects of the invention described below.

A second aspect of the invention generally features antibodies specific for human carcinoma antigen, in which the antibody is less reactive with mouse epiglycanin than with HCA. In preferred embodiments, the antibody is raised by challenging the animal with HCA or an immunodeterminant containing a fragment thereof. It is also possible to raise HCA binding antibodies by challenging an animal with anti-idiotypic antibodies described below. Preferably, the antibody requires a GalB(1→3)GalNAc chain for binding. Also preferably, the antibodies used in the invention are monoclonal antibodies.

In a third aspect, the invention generally features immunoassays to determine the presence of HCA in a biological sample by reacting the sample with an antibody that binds to HCA, preferably the monoclonal antibody, AE3, the reaction being carried out for a time and under conditions allowing the formation of an immunocomplex between the antibody and HCA. The quantitative determination of such an immunocomplex is then performed. In one version of the third aspect of the invention, the antibody used is an antibody generated by administering to a mammal (e.g., a rabbit, goat, mouse, pig, etc.) an immunogen that is HCA, an immunogenic fragment of HCA, or an anti-HCA-binding idiotypic antibody. Other versions of this aspect of the invention feature the use of HCA-binding antibodies generally (regardless of whether they are raised to one of the immunogens described above). For example a second version features a format in which immunocomplex formation is determined by competitive immunoassay procedures—i.e., the HCA-binding antibody is reacted with sample and with a competing antigen, e.g., a labeled tracer antigen or an immobilized competing antigen. A third version features a sandwich immunoassay format which uses a second antibody that also binds HCA, one of the two antibodies being immobilized and the other being labeled.

Preferred embodiments of the first version of the third aspect of the invention feature detecting an immobilized complex between HCA and an HCA-binding antibody using a second antibody that is labeled and binds to the first antibody. Alternatively, the first version features a sandwich format in which the second antibody also binds HCA. In the sandwich immunoassay procedures, HCA-binding antibody can be a capture antibody attached to an insoluble material and the second HCA-binding antibody can be a labeling antibody.

The above-described competitive immunoassay procedures or sandwich immunoassay procedures can be used with the antibodies described above in connection with the first version of the third aspect of the invention. Suitable competing antigens to be used in competitive formats for the third aspect of the invention include: HCA; immunodeterminant containing fragments of HCA; epiglycanin; or immunodeterminant containing fragments of epiglycanin. One preferred competing antigen is a fraction of epiglycanin that does not bind to peanut lectin. The competing antigen may be labeled or immobilized.

The assays of the third aspect of the invention can be used to determine HCA in samples including urine, plasma, serum, peritoneal fluid or lymphatic fluid, or solid tissue biopsies, such as breast carcinoma. This aspect of the invention also features immunoassay kits for detecting human carcinoma antigen, comprising HCA-binding antibody and the means for determining binding of the antibody to HCA in a biological sample. In preferred embodiments, the kit includes one of the second antibodies or the competing antigens described above.

A fourth aspect of the invention features methods of imaging tumors (preferably in vivo) by administering an HCA-binding antibody bound (coupled) to an imaging agent such as a radioisotope or other imaging agent.

A fifth aspect of the invention features reagents and methods for selectively labeling human tumor tissue using labeled HCA-binding antibodies bound (coupled) to detectable labels, such as enzymatic labels, fluorescent labels, stains or radioisotopes.

A sixth aspect of the invention features treating human tumors, such as breast carcinomas, by administering HCA-binding antibodies bound (coupled) to cytotoxins, such as chemotoxins (e.g., ricin) or cytotoxic radioisotopes.

A seventh aspect of the invention features HCA binding anti-idiotypic antibodies, which can be used as: a) vaccines protecting against carcinomas; b) immunotherapeutics to induce a cancer patient's immune system to generate an anti-carcinoma immune response; c) competing antigens in the above described competitive immunoassay formats; d) as a purification reagent to separate HCA-binding substances from non-HCA binding substances.

An eighth aspect of the invention features HCA formulated in a composition suitable for administration to humans, e.g., as a protective vaccine or as an immunotheraputic to induce a cancer patient's immune system to generate an anti-carcinoma immune response.

DESCRIPTION OF THE PREFERRED EMBODIMENTS

I. Sources Of HCA

Figure 1:
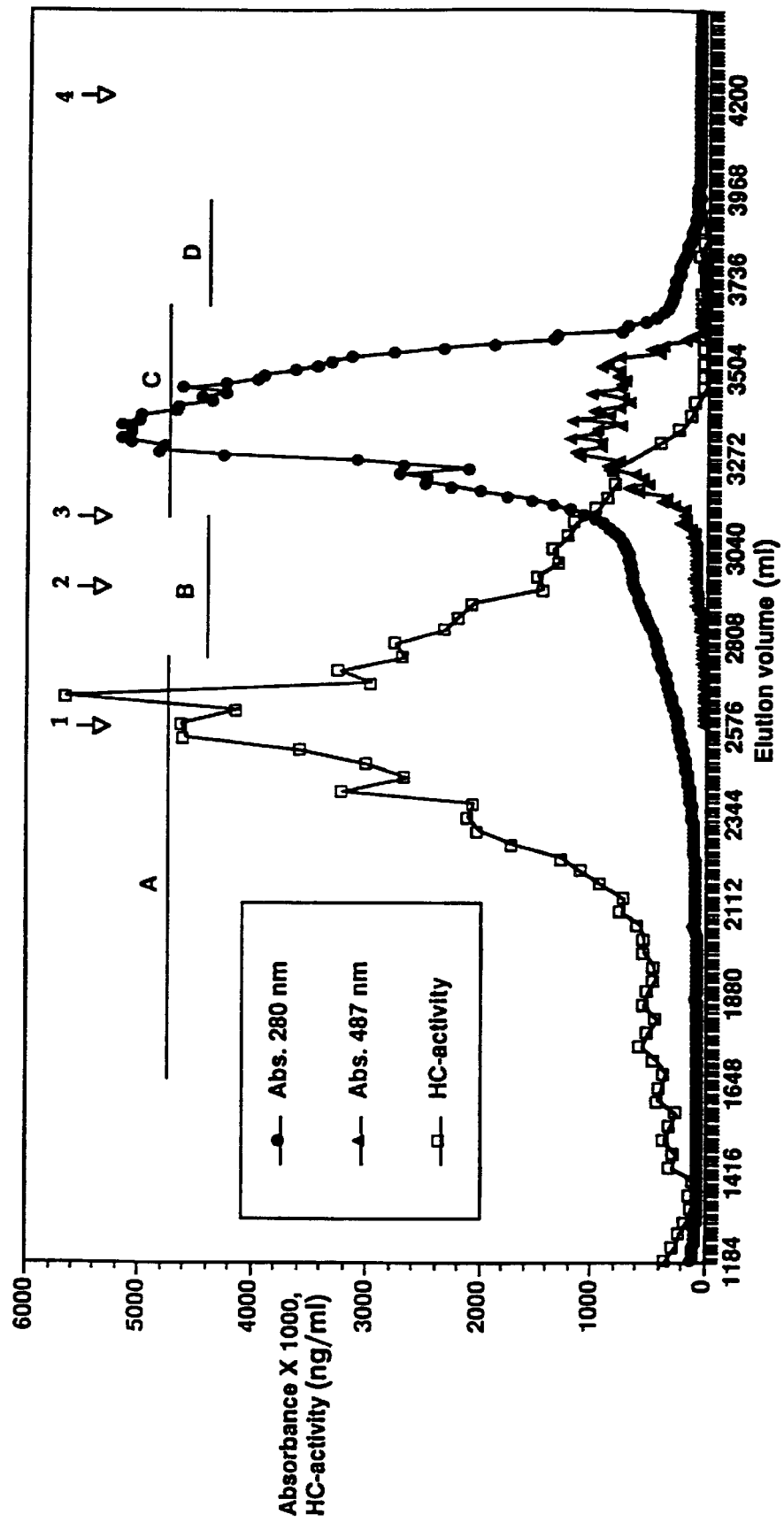
FIG. 1 is a graph related to Example 2 concerning HCA purification.

As described above, HCA is a human carcinoma antigen and can generally be obtained by culturing established human carcinoma cell lines, or from ascites fluid of carcinoma patients, particularly breast and ovarian carcinoma patients. Appropriate cell lines can be screened for HCA production using the immunoassays described below. Preferred cell lines are those producing relatively higher concentrations of HCA as determined by such assays.

One cell line source of HCA is the human endometrial carcinoma cell line KLE (ATCC accession no. CRL1622) described in Richardson et al. *Gynecologic Oncology* 17:213–230 (1984). Those skilled in the art will appreciate that there are numerous other possible cell line sources. For example, the ATCC has numerous carcinoma cell lines from various types of carcinomas, including KLE, described above.

HCA can also be isolated from fluids (pleural, peritoneal, serum, etc.) of patients with carcinomas including carcinomas of the breast, colon, prostate, ovary, lung, etc.

II. Purification Of HCA

In general, the carcinoma cell line is cultured (for example, as described by Richardson et al.), and the spent medium is concentrated, e.g. using Filtron Omega Ultrasette filtration system equipped with a 100K membrane, and its high molecular weight fraction is isolated. HCA immunoreactivity can be followed using an anti-HCA antibody described below, or using anti-epiglycanin antibodies such as AE-3, described above and reported in Codington U.S. Pat. No. 4,837,171. The substantial majority of the HCA immunoreactivity is retained in the high molecular weight fraction.

The high molecular weight fraction is subjected to further chromatography, e.g. Sepharose CL-2B. Again, the majority of the HCA immunoreactivity will be in the highest molecular weight range (1–2 million molecular weight).

Further chromatography (e.g. Mono P coupled to a Pharmacia FPLC system) is performed on the resulting high molecular weight fraction. HCA activity is followed by immunoassay, e.g., with an enzyme linked competitive binding assay. HCA tends to precipitate on the Mono P column as an insoluble precipitate that is not effectively removed by NaCl gradient. This precipitate is substantially insoluble in solutions of urea, dithiothreitol, guanidine hydrochloride, or perchloric acid.

III. Obtaining Immunodeterminant Containing HCA Fragments

Because of the extraordinary size and insolubility of native HCA, it is usually convenient to work with immunodeterminant-containing HCA fragments. Such fragments are prepared by partial proteolytic degradation (e.g. using an enzyme such as TPCK-trypsin, Pronase™, or pepsin). The digest can be purified by chromatography, e.g. gel exclusion, collecting fractions having HCA immunoreactivity.

IV. Antibodies To HCA

HCA recovered as described above, or fragments of it, can be used as an immunogen to challenge a mammal, e.g. a mouse, rabbit, rat or goat. Those skilled in the art will recognize that various protocols may be used. Preferably, protocols used in producing anti-epiglycanin antibodies (described below) can be used to make anti-HCA monoclonal antibodies. Preferably the animal is challenged over a substantial period (e.g. 5 months). See generally, Haavik et al., (1992) *Glycobiology* 2:217–224. For mouse monoclonal antibodies, standard fusion partners may be used to immortalize spleen cells from the challenged animal. See, e.g., Kohler and Milstein, (1977) *Nature* 256:495–497. The resulting anti-HCA monoclonal antibodies or polyclonal antibodies may be used in the various immunological procedures described below.

V. Immunoassays For HCA

Immunoassays for HCA can be performed using the anti-HCA antibodies described above or other HCA-binding antibodies such as anti-epiglycanin antibodies that bind HCA. In general, any suitable immunoassay format can be used. For example, an immobilized HCA/anti-HCA antibody complex can be formed (by radioimmunopreciptation) and detected with antibody specific for the anti-HCA antibody. Thus, if the HCA-binding antibody is a mouse-generated antibody, the immunocomplex may be detected with a labeled goat anti-mouse antibody. We use the term labeling generally to describe all types of well known labels such as enzymes (e.g., horseradish peroxidase) or other suitable labels, including radiolabels, fluorophores, and chromophores. Biotin/avidin labeling systems may be used.

In a competitive format (e.g. as described in example 18) it is possible to use a competing antigen that is labeled or immobilized. It is particularly important in a competitive format to use a suitable competing antigen. One preferred competing antigen features a fraction of epiglycanin known as epiglycanin-A, obtained as described below. (Example 17)

Best results are obtained by the addition of serum first, then monoclonal antibody, to the wells. Less satisfactory results are obtained if the two components are mixed prior to their addition to the wells. It is also important that the addition of serum and antibody be completed within a short period of time (i.e., about 30–50 min).

The PBS used in this competitive assay is at pH 7.5–7.6 and contains three times the concentration of phosphate that is generally used in immunoassays, in order to minimize variability in the assay due to pH changes.

When performed under optimal conditions, the competitive binding assay may be used to quantitatively determine the concentration of HCA present in the blood (serum or plasma) of individuals with carcinomas. The preferred procedure embodies the following steps.

The wells of a 96 well microtiter immunoplate are coated by adding 100 $\mu$l of a solution of Epiglycanin A in PBS (7.5 ng/ml) and allowing this solution to stand for 15–20 hours at 4° C. Alternatively, the coating solution may be allowed to dry in the wells. Such plates may be stored in the dry state for several weeks at 4° C. After discarding the coating solution, the wells are blocked with Superblock (Pierce Chemical Co., 275 $\mu$l/well) for 60 min. at 4° C. They are washed with PBS containing Tween 20 (0.05%), a solution used for all washes. The addition of 50 $\mu$l of sample to be assayed (i.e., serum at full strength, HCA standards, other HCA-containing material, or controls) is quickly followed by the addition of 50 $\mu$l of antibody. The optimal concentration range for HCA is approximately 1–200 ng/ml. Monoclonal antibody is used at a concentration of 200 ng/ml (10 ng/well). All dilutions are made in a Superblock solution, and each sample is assayed in triplicate.

The plate is incubated for 14–20 hours, then washed as before. After the addition of 100 $\mu$l of goat anti-mouse IgM, coupled to horseradish peroxidase (1:3000 in PBS), the plate is incubated for 2.0 hours at 4° C., then washed. The concentration of HCA is correlated with the amount of bound antibody. Antibody concentration is determined by the addition of substrate [2,2'-Azino-bis(3-ethylbenzthiazoline-6-sulfonic acid) (ABTS) at a concentration of 1 mg/ml citrate buffer], with 1 $\mu$l/ml of 30% $H_2O_2$. Color develops at 20°–25° C. and is read using a spectrophotometer at 405 nm.

These assays can be used to: a) determine the presence of a carcinoma initially; b) to stage the carcinoma and thus provide guidance for future treatment (systemic versus localized treatment); c) to follow a course of treatment of a carcinoma; and (d) determine recurrence of a carcinoma.

VI. In Vivo Imaging Using Anti-HCA Antibodies

Anti-HCA antibodies can be used to specifically image tumors, in vivo. For example, the antibodies can be covalently bound to radioisotopes suitable for in vivo imaging, such as $^{111}$In or $^{99m}$Tc. Less favored is $^{131}$I. Those skilled in the art will understand that there are numerous well known techniques for generating the radioisotopes at issue and binding the radioisotopes to antibodies. See, for example, Bartorelli, U.S. Pat. No. 4,732,862 hereby incorporated by reference regarding radioisotope labeling of antibodies. See also, Goldberg et al., (1978) *New England J. Med.* 298:1384 et seq.; Seragini et al., (1989) *Clin. Nucl. Med.* 14:580–587; and Surwit, (1990) *Antibody, Immunoconjugates, and Radiopharmaceuticals* 3:48–49 regarding preparation of radiolabeled antibodies. Kits for radiolabeling can be obtained, e.g., from various commercial sources, such as Amersham, Mediphysics, Syncor, or Mallinckrodt.

Those skilled in the art will also understand that the imaging agent described above can be administered (infused) by various well known techniques, such as injection at a specific site or by i.v. infusion. See, e.g., Treves, U.S. Pat. No. 4,729,380. Readings are taken by standard techniques such as a body scanning scintigram using a gamma camera interfaced with a computer.

VII. Tissue Staining Using HCA-Binding Antibodies

Anti-HCA antibodies or HCA-binding antibodies can be coupled (bound) to imaging agents such as the radioisotopes described above or other imaging agents such as fluorescent imaging agents, and visual imaging agents (stains). See, e.g., Kortright U.S. Pat. No. 4,708,930, cited above. Standard techniques are used to obtain tissue sections and to label them with HCA-binding antibodies that are coupled to an appropriate label. Another technique involves the use of electron microscopy (electron dense) imaging agents (e.g., gold [particles).

VIII. Cell-Selective Immunotherapeutics

To destroy the tumor cells, HCA-binding antibodies are coupled to cytotoxic agents such as ricin A chain, abrin A-chain, modeccin A-chain, gelonin, melphalan, bleomycin, adriamycin, daunomycin, or pokeweed antiviral proteins (PAP, PAPII, PAP-S). Those skilled in the art will realize that there are numerous radioisotopes or chemocytotoxic agents that can be coupled to tumor specific antibodies by well known techniques, and delivered to specifically destroy tumor tissue. See, e.g., Blattler et al. U.S. Pat. No. 4,542,225.

IX. Anti-idiotypic Antibodies

Those skilled in the art will realize that known techniques can be used to raise anti-idiotypic antibodies, e.g., idiotypic antibodies that will bind to HCA-binding antibodies. HCA-binding anti-epiglycanin antibodies or anti-HCA antibodies can be used as immunogens to challenge a mammal according to the immunization regime described above for anti-HCA antibodies. See. e.g., Hellstrom et al., in U.S. Pat. No. 4,918,164, cited above. The resulting anti-idiotypic antibodies can be used as: a) vaccines to induce an immune response resulting in protection against the development of carcinomas; b) immunotherapeutics to induce a cancer patient's immune response to his carcinoma; c) competing antigens in the above described competitive immunoassay formats; d) as purification reagents to separate HCA-binding substances from non-HCA binding substances.

For in vivo applications, those skilled in the art will recognize that there are various known techniques to make mouse monoclonal antibodies more compatible with human therapies, e.g., Winter et al., (1991) *Nature* 349:293–299; Sahagan et al., (1986) *J. Immunol.* 137:1066–1074; and Boss et al., U.S. Pat. No. 4,816,397.

IX. HCA-Based Vaccines And Immunotherapeutics

Those skilled in the art will recognize that HCA (or immunodeterminant fragments of it) purified as described above, can be formulated as a vaccine, using standard vehicles such as pyrogen free buffered saline. The vaccine can be administered by standard techniques (e.g., i.v.) over a suitable course of treatment to induce an anti-carcinoma immune response. Such a response can be prophylactic or therapeutic (for patients already diagnosed as having a carcinoma).

X. Specific Examples

The following specific experiments are provided to illustrate the invention, without limiting its scope.

EXAMPLE 1
Filtration of Spent Medium From Cultured Carcinoma Cell Line

The KLE endometrial carcinoma cell line referenced above was cultured as generally described by Richardson et al. (1984). Generally, the cells were grown in medium containing equal volumes of Ham F12 and Dulbecco's Modified Eagle's Medium with 15% fetal calf serum (GIBCO), 60 mU/mL insulin, 20 U/mL penicillin, 20 $\mu$g/mL streptomycin and 0.5 $\mu$g/ml amphotericin. Samples of spent medium from cultures with confluent cells were withdrawn and spun. The spent medium was concentrated by a Filtron omega Ultrasette, equipped with a 100K membrane (4° C.), and the high molecular weight fraction was tested for HC-antigen content by the enzyme competitive binding assay, as described below.

EXAMPLE 2
Gel Filtration Chromatography on a Sepharose CL-2B Column

Samples of concentrated medium described in Example 1 were subjected to gel filtration chromatography on a column (5×180 cm) of Sepharose Cl-2B eluted with PBS buffer pH 7.50. Fractions were collected and assayed for carbohydrate by the general phenol-sulfuric acid method of Dubois et al. (1956) *Anal. Chem.* 28:350–356, and the absorbance was read at 490 nm. The collected fractions were assayed for HC-antigen content using the enzyme competitive binding assay described below. After 10 chromatographic runs (of 3 days each) fractions were pooled. Fraction A was concentrated by the Filtron Ultrasette with an Omega 100K membrane and kept stored at −20° C. until it was subjected to further purification and characterization.

Specifically, FIG. 1 shows the results of chromatography on two coupled columns of Sepharose CL-2B (5×90 cm each). Fractions were tested for reactivity to HCA-binding antibodies, and for protein and carbohydrate content as described below. Elution volumes of molecular weight markers are indicated by arrows: 1: Dextran T 2000 (2,000,000); 2: Thyroglobulin (670,000); 3: Bovine serum albumin (BSA) (67,000); 4: $K_2Cr_2O_7$ (294). Fractions A, B, C and D were pooled as indicated.

EXAMPLE 3
FPLC Ion Exchange Chromatography on Mono P Column

Samples of fraction A from the Sepharose CL-2B column (Example 2) were applied to a column of Mono P (Pharmacia) (10×300 mm) coupled to a Pharmacia FPLC system. The column was eluted with a gradient of sodium chloride in 15 mM phosphate buffer pH 7.20. The absorbance at 280 nm of the eluate was monitored and fractions collected and tested for activity binding to HCA-binding antibodies by the enzyme competitive binding assay as described below.

Figure 2:
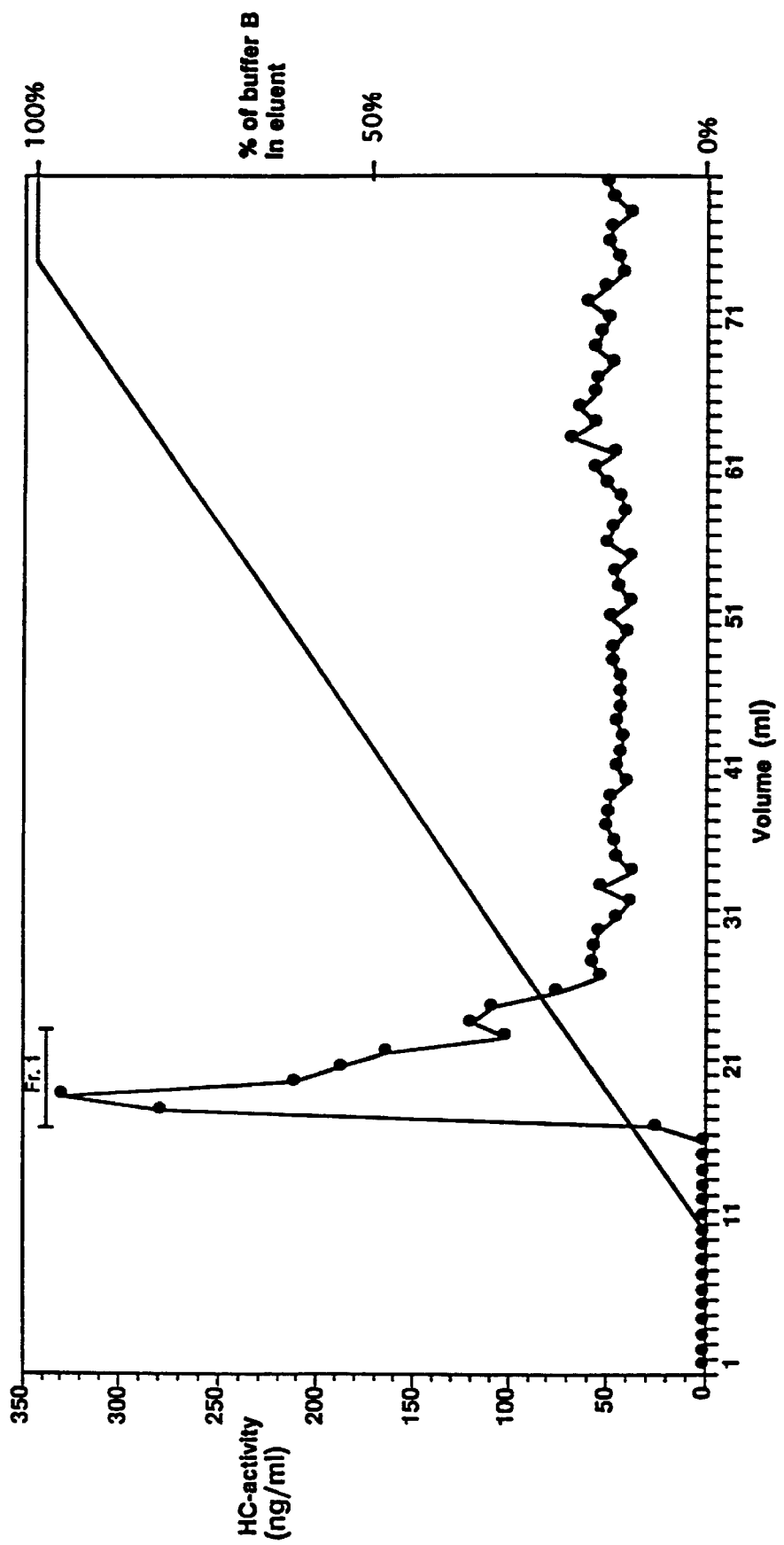
FIG. 2 is a graph related to Example 3 concerning HCA purification.

FIG. 2 shows the absorbance of the effluent.

EXAMPLE 4
Redissolving HCA

Samples of suspended precipitate of Fr. A (Example 3) were incubated with either 2M urea, 4M urea, 2% dithiothreiothol, 2% EDTA, 4M guanidine hydrochloride for 16 h at room temperature. The samples were then tested for binding activity to HCA-binding antibodies by the enzyme competitive binding assays as described below. Substantially no HCA activity was found in the solutions.

EXAMPLE 5
Fragmentation of HCA

Figure 3:
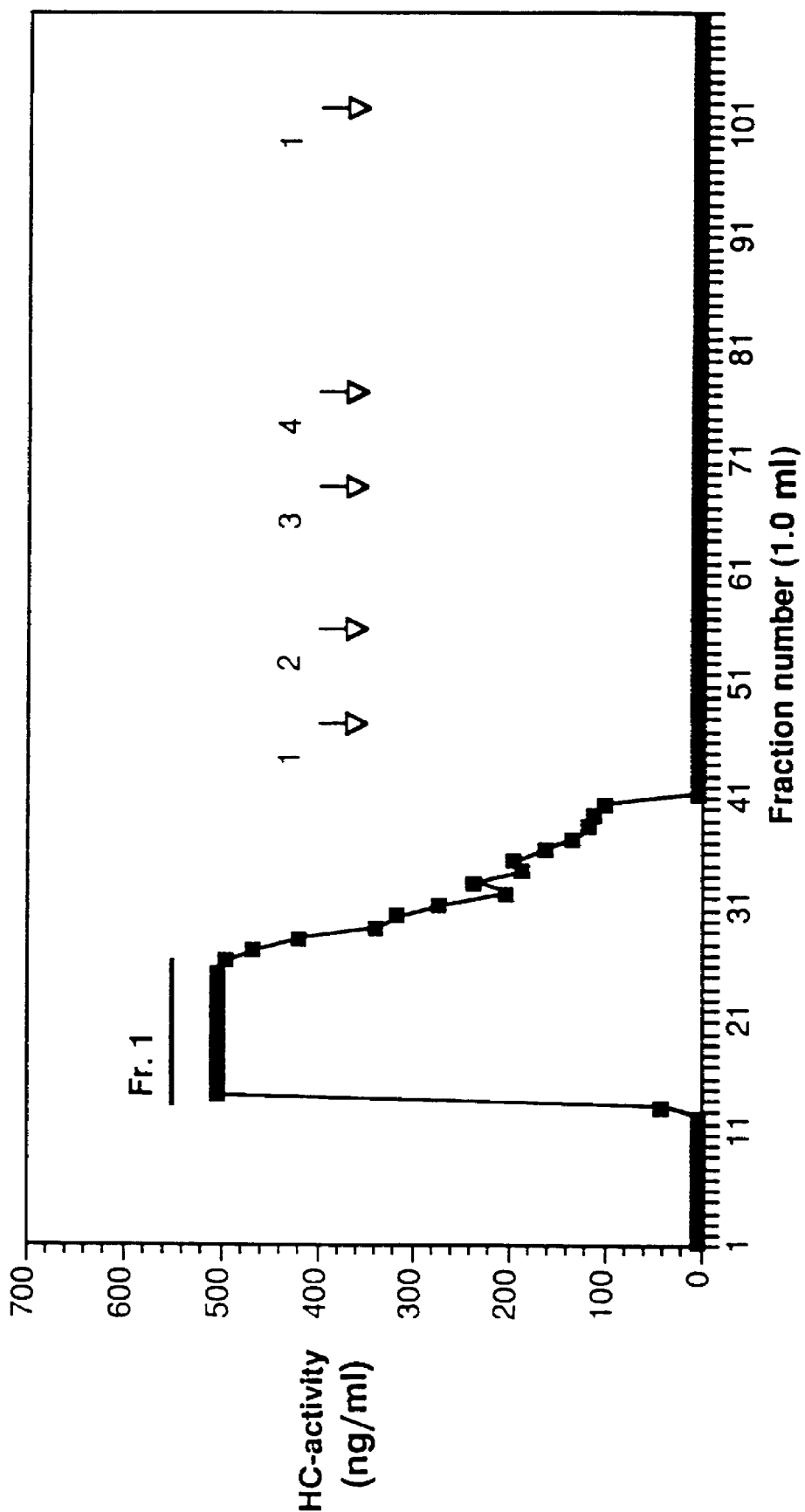
FIG. 3 is a graph related to Example 5 concerning fragmentation of HCA.

Suspensions of Fr. 1 (Example 3) were incubated with 20 $\mu$g/mL TPCK-trypsin in 0.1M sodium phosphate buffer pH 6.80 for 16 h at 37° C. The incubation mixtures were then applied to a Superdex 200 (10×600 mm) column and eluted 1.0 mL/min with 0.1M sodium phosphate buffer containing 0.15M NaCl. The absorbance at 280 nm was monitored, and fractions were collected and tested for binding activity to HCA-binding antibodies as described below. FIG. 3 depicts the absorbance of the effluent at 280 nm. Elution volumes of molecular-weight-markers are indicated: 1: Dextran T 500 (500,000); 2: Thyroglobulin (670,000); 3: Aldolase (158,000); 4: Bovine serum albumin (BSA) (67,000); 5: Ribonuclease A (13,700).

Figure 4:
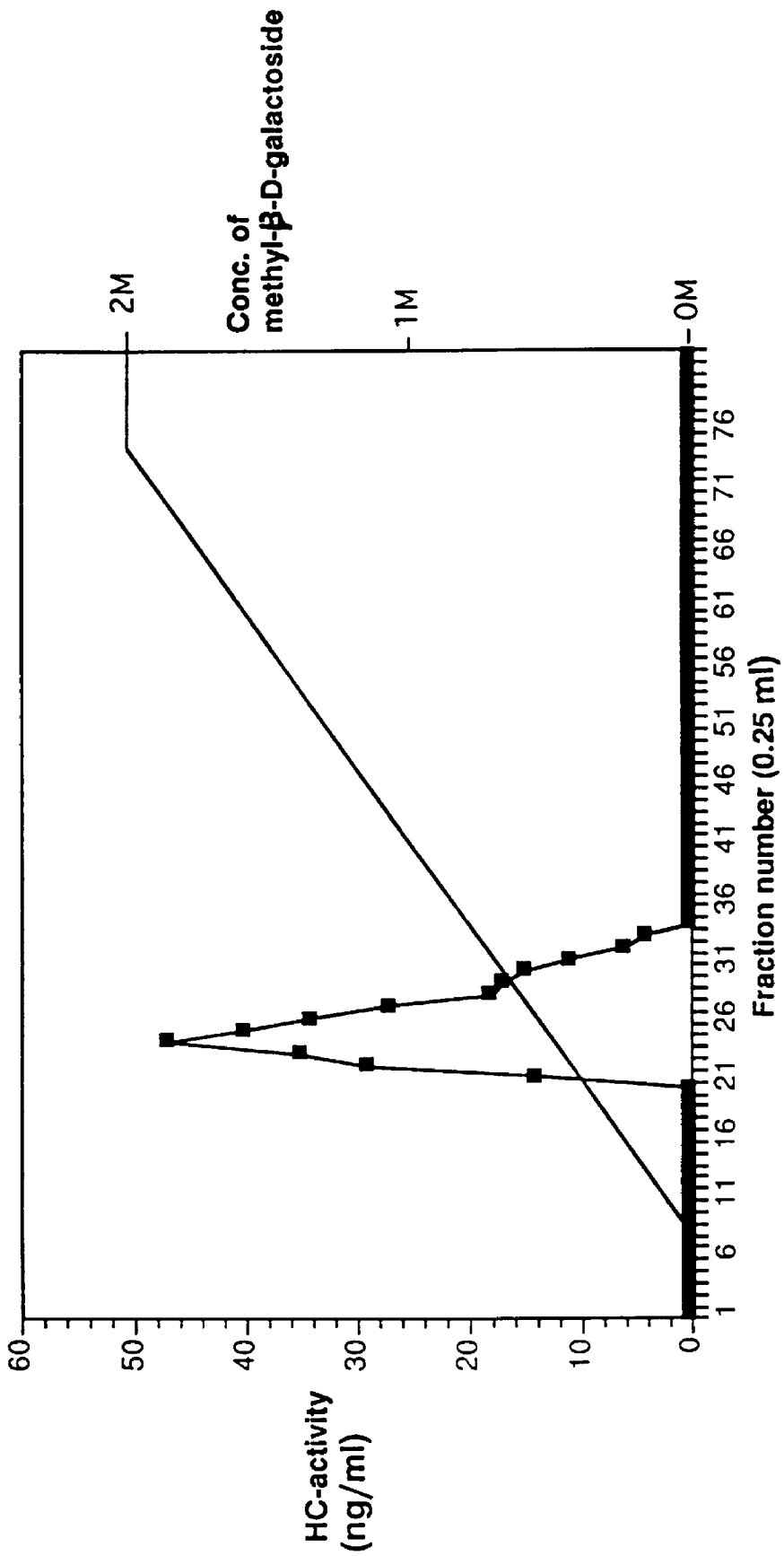
FIG. 4 is a graph related to Example 6 concerning purification of HCA fragments.
Figure 5:
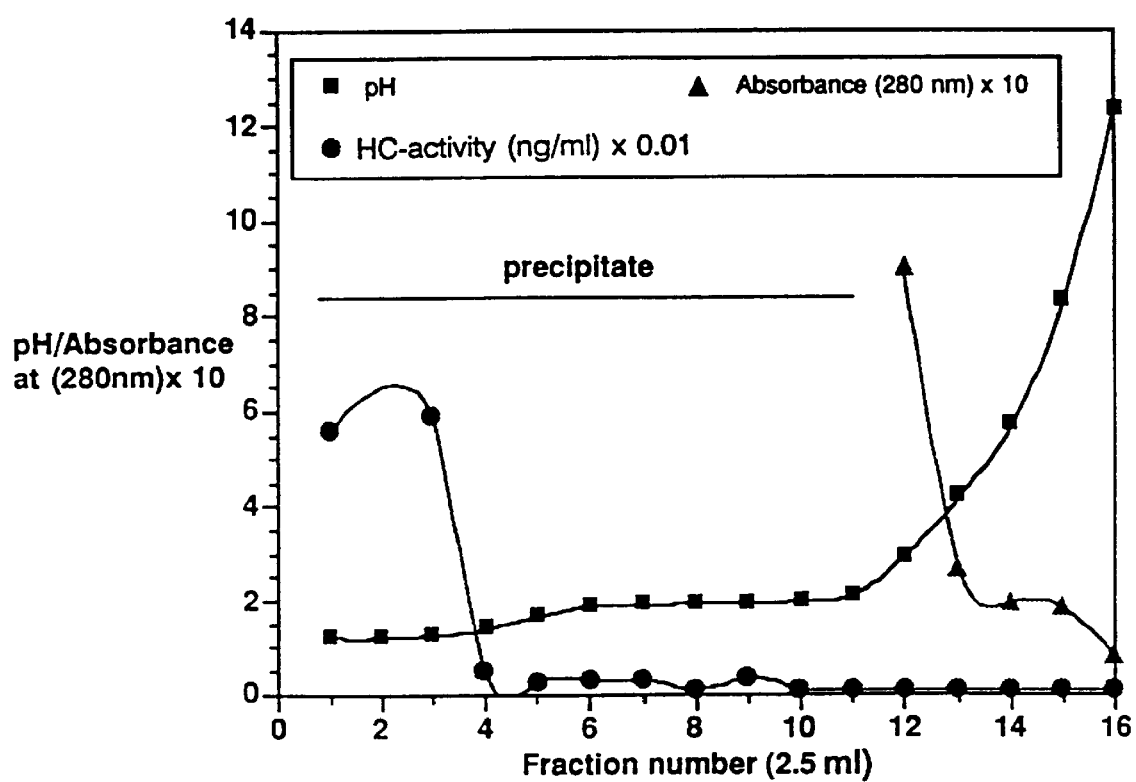
FIG. 5 is a graph related to Example 10.
Figure 6:
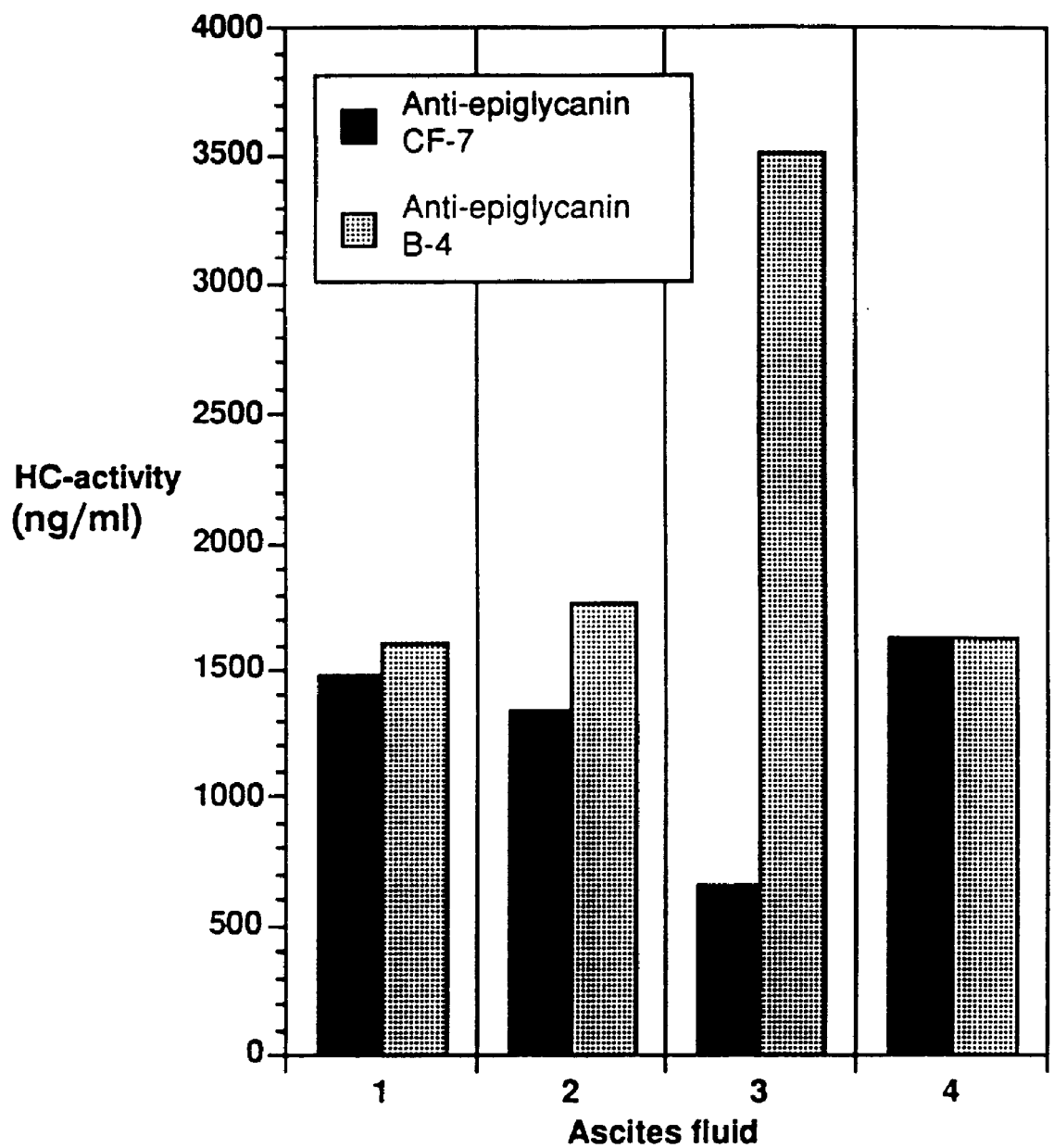
FIG. 6 is a graph related to Example 12.
Figure 7:
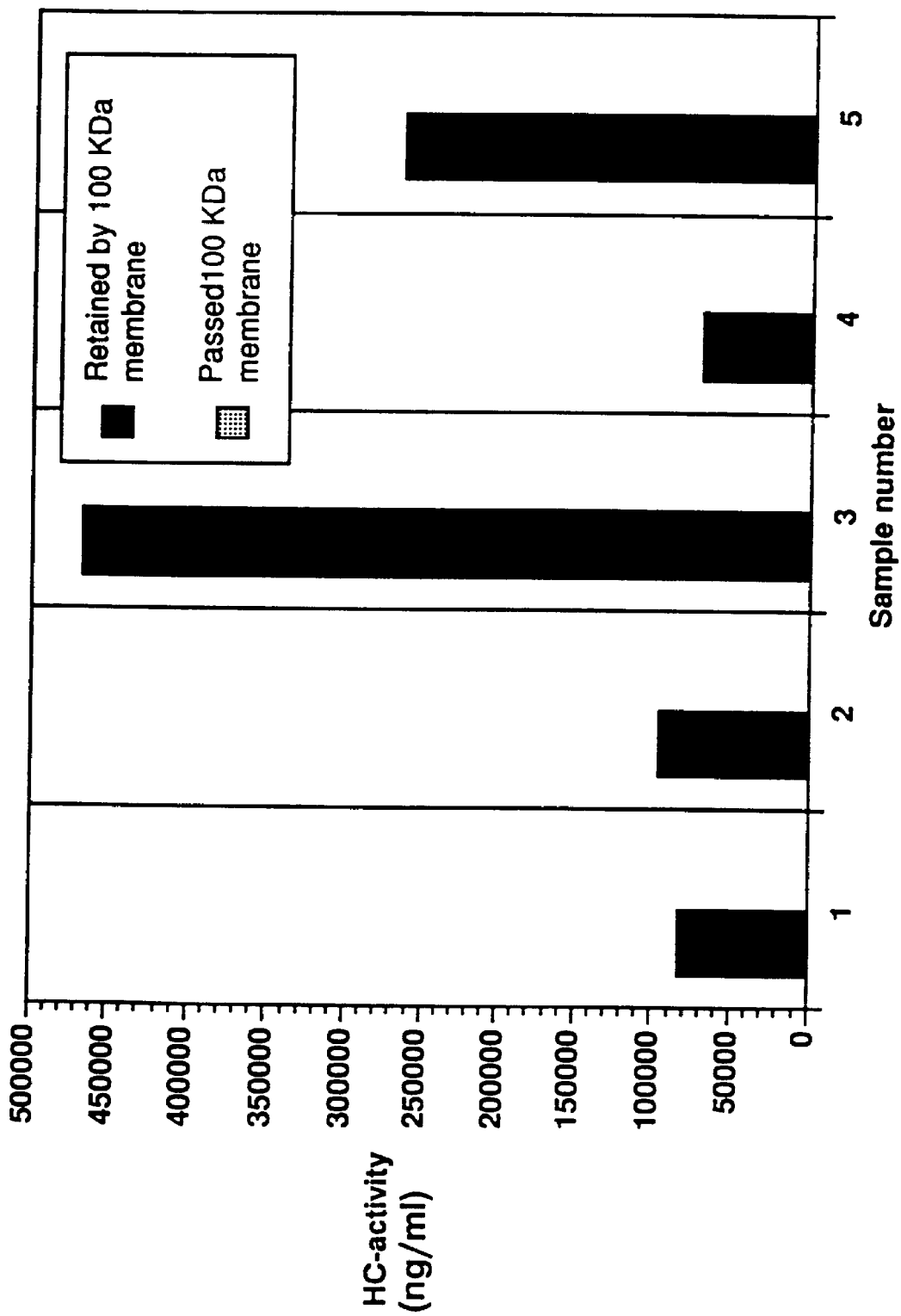
FIG. 7 is a graph related to Example 13.

EXAMPLE 6
Affinity Chromatography on a Column of Peanut Aggalutinin Sepharose A sample of Fr. 1 from the Superdex 200 column (Example 5) was applied on a column (10×50 mm) of *Arachis hypogea* lectin insolubilized on 4% beaded agarose (Sigma). The column was eluted at 0.1 mL/min with: a) 0.1M Na-phosphate buffer pH 6.8 containing 0.2M NaCl; b) a gradient of 0–2M methyl-β-D-galactopyranoside in 0.1M Na-phosphate buffer pH 6.8 containing 0.2M NaCl. The absorbance at 280 nm was monitored, fractions collected and tested for binding activity to HCA-binding antibodies by the enzyme biotin sandwich assay as described below. FIG. 4 depicts absorbance of the effluent at 280 nm.

EXAMPLE 7
Evaluation of HCA Epitopes

Samples of Fr. A from the Sepharose CL-2B column of the spent KLE medium (Example 1) were subjected to either periodate oxidation (10 mM NalO$_4$ at pH 4.0 for 30 min at 20° C.), incubation at 37° C. for 16 h with TPCK-trypsin, neuraminidase (*Vibrio cholera*, type II), or endo-α-N-acetyl-D-galactosaminidase (O-Glycanase). The samples were then diluted and tested for HC-activity by the enzyme competitive binding assay. The above reagents altered binding activity for an HCA-binding antibody as follows: Neuraminidase 19%—activity remaining; endo-N-acetyl-galactosaminidase—activity remaining 0.1%; periodate (10 mM, 20° C., 1h)— activity remaining 10%; TPCK-trypsin—activity remaining 137%.

EXAMPLE 8

Enzyme Competitive Binding Assay For Non-Serum Samples

To the wells of a Nunc Maxisorp 96 well plate were added 100 $\mu$l of epiglycanin (50 ng/mL) in PBS, pH 7.50, and incubated for 16 h at 4° C. The wells were blocked by incubation for 45 min with 0.5% BSA in PBS, pH 7.50 (PBS-BSA). Two solutions were added: a) 50 $\mu$L of a standard solution of epiglycanin (1–200ng/ml) or sample; and b) 50 $\mu$L of purified monoclonal anti-epiglycanin IgM (dilution 1: $OD_{280}$×10,000). Both antibody and antigen were diluted with PBS-BSA. The mixture was incubated on a shaker for 16 h at 20° C. The wells were washed three times (Skatron microplate washer) with PBS containing 0.05% Tween 20 and incubated for 2 h at 20° C. with alkaline phosphatase labeled goat anti-mouse IgM dissolved in PBS-BSA. The wells were washed three times and then 100 $\mu$L substrate solution containing 1 mg/mL p-nitrophenyl phosphate in 0.1M ethanolamine pH 10.0 was added. The absorbance was read at 405 nm in a Bio-Rad Microplate reader coupled to a Macintosh SE computer using the Microplate Manager TM program.

EXAMPLE 9

Enzyme Biotin Sandwich Assay

To the wells of a Nunc Maxisorp U 96 microtiterplate were added 100 $\mu$L monoclonal anti-EPGN antibody (2 $\mu$g/mL) diluted in PBS pH 7.50 and incubated for 16h at 40° C. The coating solution was then removed and the wells were blocked by incubation for 45 min with 200 $\mu$L 0.5% BSA in PBS, pH 7.50 (PBS-BSA) at 4° C. After the blocking solution was removed, 100 $\mu$L solutions of epiglycanin standard or samples were added to each well. After incubation for 2 hours at 20° C., they were emptied and washed twice with 200 $\mu$L PBS pH 7.50 containing 0.05% Tween 20 (PBS/Tween) (Skatron Plate washer). 100 $\mu$L of a solution of biotinylated anti-epiglycanin antibody (1 $\mu$g/ML) diluted in PBS-BSA was added to each well and the mixture incubated for 2 h at 20° C. The wells were emptied and washed twice with 200 $\mu$L PBS/Tween. 100 $\mu$L of a solution of streptavidin-peroxidase diluted 1:5000 in PBS-BSA was added to each well and incubated for 2 hours at 20° C. The wells were emptied and were washed three times with 200 $\mu$L PBS/Tween. 100 $\mu$L of a freshly prepared solution containing 1 mg/mL O-phenylene diamine and 0.5 $\mu$L/mL $H_2O_2$ (30%) in citrate-phosphate buffer (pH 5.9) was added to each well. The plate was incubated at 20° C. until appropriate color developed, after which 50 $\mu$L 0.3M citric acid was added to the wells to stop the reaction. Absorbance was read at 490 nm in a Bio-Rad microplate reader using the Microplate Manager TM program for calculation of concentrations.

EXAMPLE 10

Isoelectric Focusing

Isoelectric focusing of HCA isolated from the ascites fluid of a patient with ovarian carcinoma was achieved as follows.

Focusing was performed in Rotofor™ Cell (Bio-Rad) for 4 h at 12 W with Biolyte 3–10 ampholyte.

Isoelectric focusing of HCA from cultured endometrial carcinoma cell lines was performed in Rotofor™ Cell (Bio-Rad) for 4 h at 12 W with Biolyte 3–10 ampholyte. FIG. 5 depicts the results of this experiment.

EXAMPLE 11

Epiglycanin Monoclonal Antibodies

Anti-epiglycanin monoclonal antibodies were prepared as described previously (Codington, U.S. Pat. No. 4,837,171; Haavik et al., 1992 Glycobiology). Briefly C57BL/J mice were immunized by subcutaneous injections of $10^6$ viable TA3-Ha ascites cells and boosted with purified epiglycanin. Spleen cells of the immunized mice were fused with BALB/c (NS1) mouse myeloma cells, as described by others. Hybridomas producing antibodies against epiglycanin were screened by an antibody capture assay using microtiterplates coated with purified epiglycanin. The antibodies were purified as described previously (Haavik et al., 1992 Glycobiology. One specific purification technique involves elution from an Avid A1 affinity column (9×20 mm, Bio Probe) followed by successive HPLC fractionations on an $AB_x$ column (7.75×100 mm, J. T. Baker) and a Protein Pak™ DEAE 5PW column (7.5×75 mm, Waters).

EXAMPLE 12

HCA in Ascites

Ascites fluid from carcinoma patients was obtained by standard techniques and measured with the competitive immunoassay described below, using two anti-mouse epiglycanin monoclonal antibodies. The results are shown in FIG. 6. Results with one antibody are shown with solid bars and with the other antibody are shown with a stippled bar. In FIG. 6 the patients had been diagnosed as follows: #1=breast carcinoma; #2=ovarian carcinoma; #3=breast carcinoma; and #4=ovarian carcinoma.

EXAMPLE 13

HCA from Ascites

HCA activity of ascites fluids of patient #4 of Example 12 and spent medium from an endometrial carcinoma cell line were concentrated by Filtron Diaflo membrane with a molecular weight cutoff of 100,000. HCA activity was tested using an anti-epiglycanin monoclonal antibody in a competitive binding assay. The results are shown in FIG. 7. Most of the HCA activity was found in the fraction retained by the membrane. HCA activity in the fraction which passed through the membrane was too low to be visible on the graph shown in FIG. 7.

EXAMPLE 14

Further Purification and Fragmentation

The concentrated ascites fluid was subjected to Sepharose CL-2B gel filtration and the material was concentrated using a Filtron Ultrasette (Filtron Technology Corporation, Northborough, Mass.) with a molecular weight cutoff limit of 100,000 Da. Specifically, the concentrated ascites fluid was applied to a column of Sepharose CL-2B (5×180 cm) (previously equilibrated in phosphate buffered saline (PBS) (pH 7.50)) at a rate of 1 ml/min. Fractions were collected and assayed for carbohydrate by the phenol-sulfuric acid method (Dubois et al., 1956) and the absorbance read at 490 nm. The determination of the approximate protein concentration in the chromatographic profiles was done by measurement of the absorbance at 280 nm in a UV-visible recording spectrophotometer, model UV-160A from Shimadzu. The absorbance was read against PBS buffer as a reference. The collected fractions were assayed for HC-antigen content using enzyme competitive binding assay with 4 monoclonal anti-epiglycanin antibodies. The fractions were pooled after 13 chromatographic runs. Fraction A was concentrated by the Filtron Ultrasette with an Omega 100K membrane, and kept stored at −20° C. until further purification.

Figure 8:
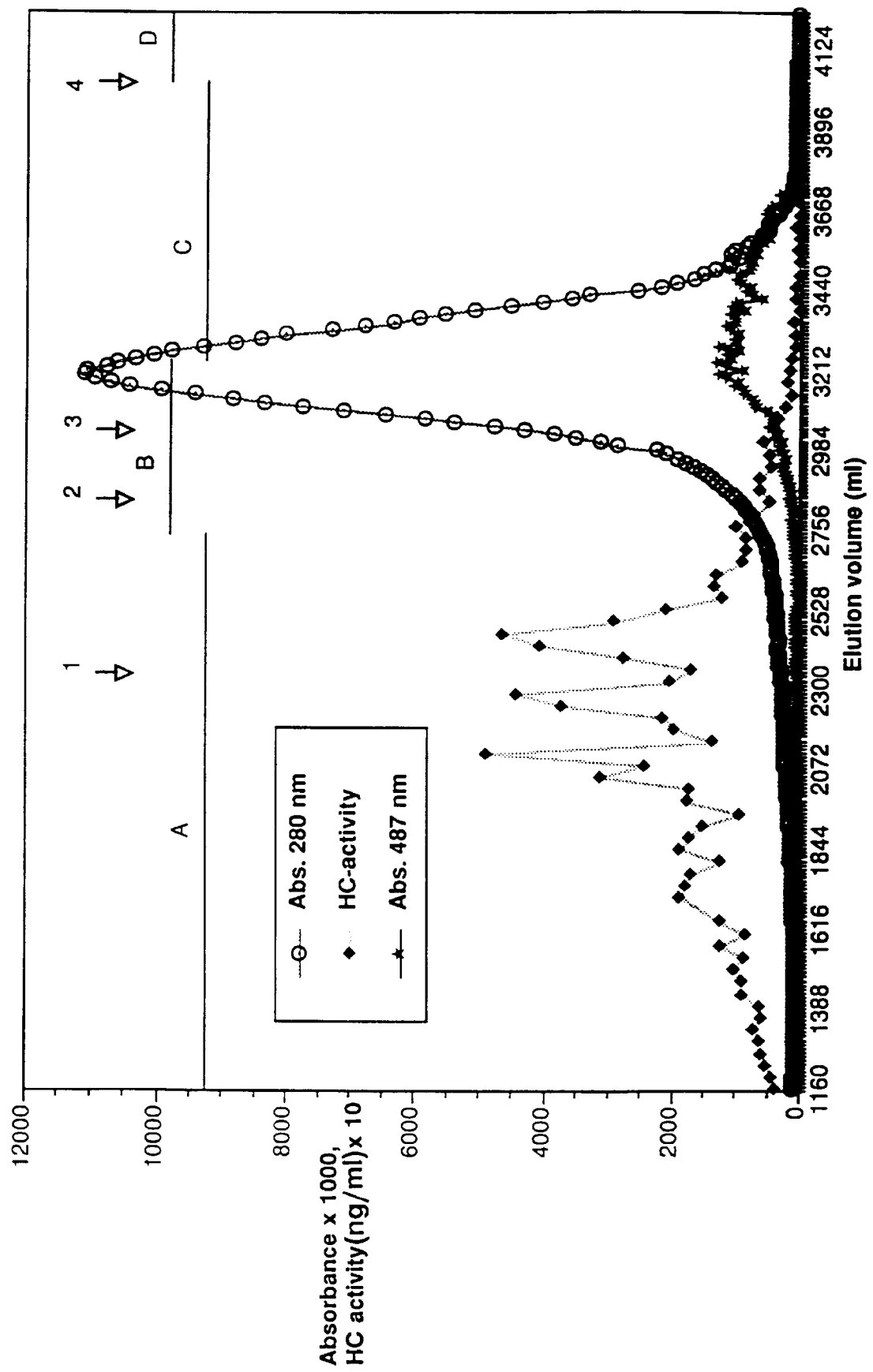
FIG. 8 is a graph related to Example 14.

The results are shown in FIG. 8. Elution volumes of molecular weight markers are indicated: 1: Dextran T 2000 (2,000,000); 2: Thyroglobulin (670,000); 3: Bovine serum albumin (67,000); 4: K2Cr207 (294). The fractions were pooled as indicated.

EXAMPLE 15
Fragmentation and Further Column Chromatography

In order to digest the HCA, an equivalent volume of TPCK-trypsin (40 μg/ml) in 0.1M sodium phosphate buffer pH 6.8 was added to an HCA suspension and incubated for 16 h at 37° C.

The concentrated and trypsin-digested fraction A eluted from the Sepharose CL-2B column was applied to a column of Superdex 200 HR 16/60 column (10×600 mm) coupled to an HPLC-instrument. The column had been equilibrated with 0.1M sodium phosphate buffer (pH 6.8) containing 0.2M NaCl, and was run at a flow rate of 1.0 ml/min. Fractions of 1.0 ml were collected. The absorbance at 280 nm of the effluent was monitored and fractions collected and assayed for HC-antigen content by the enzyme competitive binding assay as described above.

Figure 9:
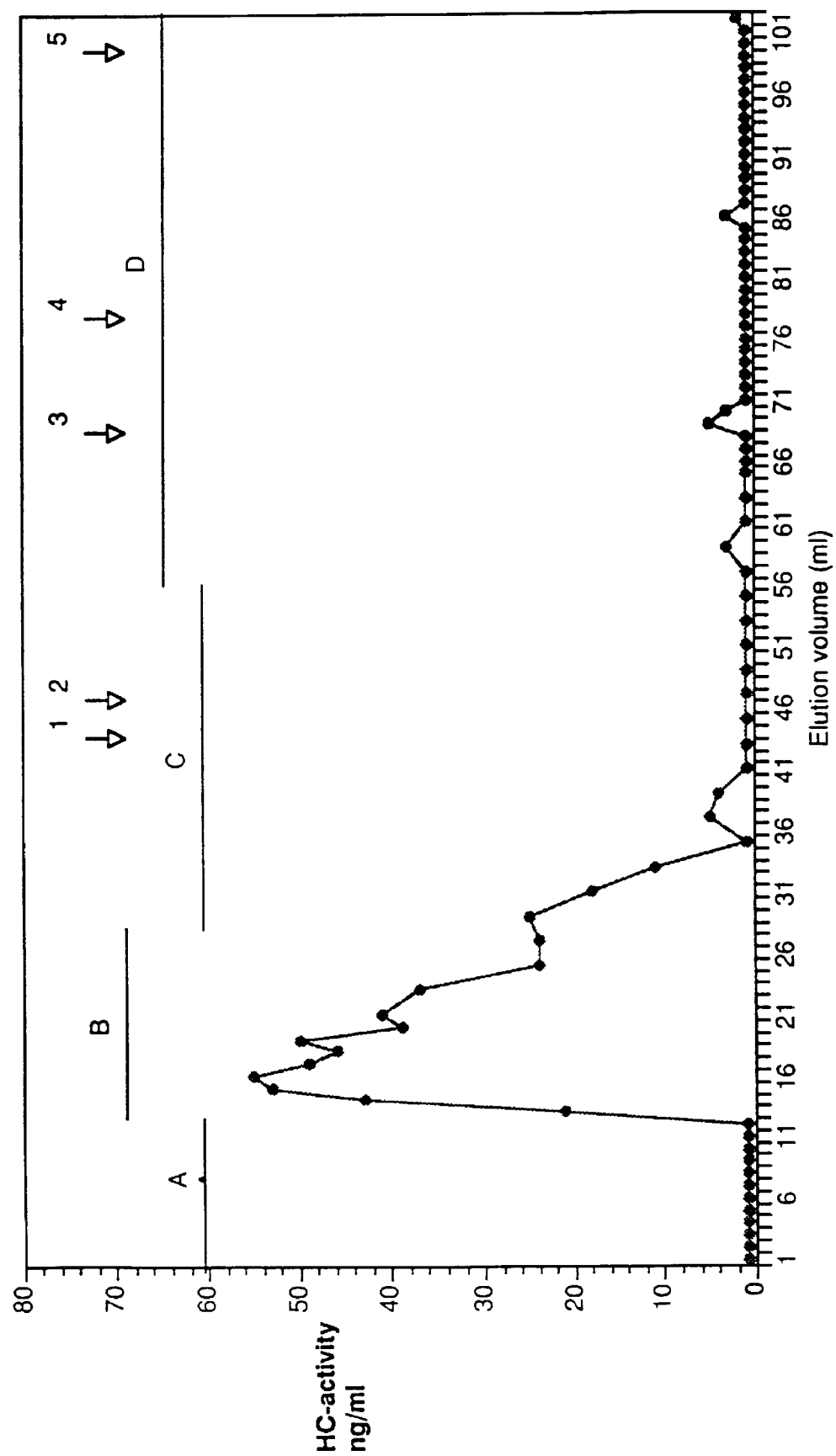
FIG. 9 is a graph related to Example 15.

The results are described in FIG. 9. Elution volumes of molecular weight markers are indicated: 1: Dextran T 500 (500,000); 2: Thyroglobulin (670,000); 3: Aldolase (158,000); 4: Bovine serum albumin (67,000); 5: Ribonuclease A (13,700). The fractions were pooled as indicated.

EXAMPLE 16
pH-Dependent Precipitation of HCA from Human Ascites Fluid

Figure 10:
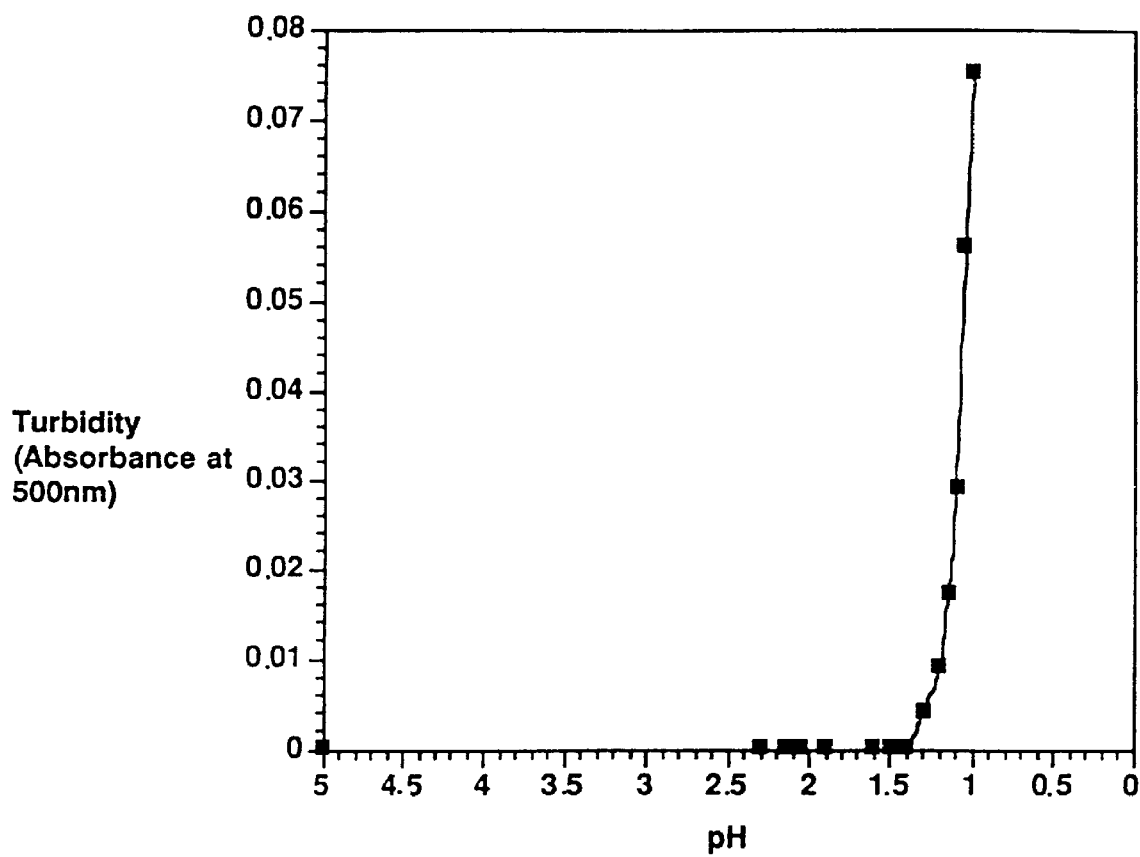
FIGS. 10–12 are graphs related to Example 16.
Figure 11:
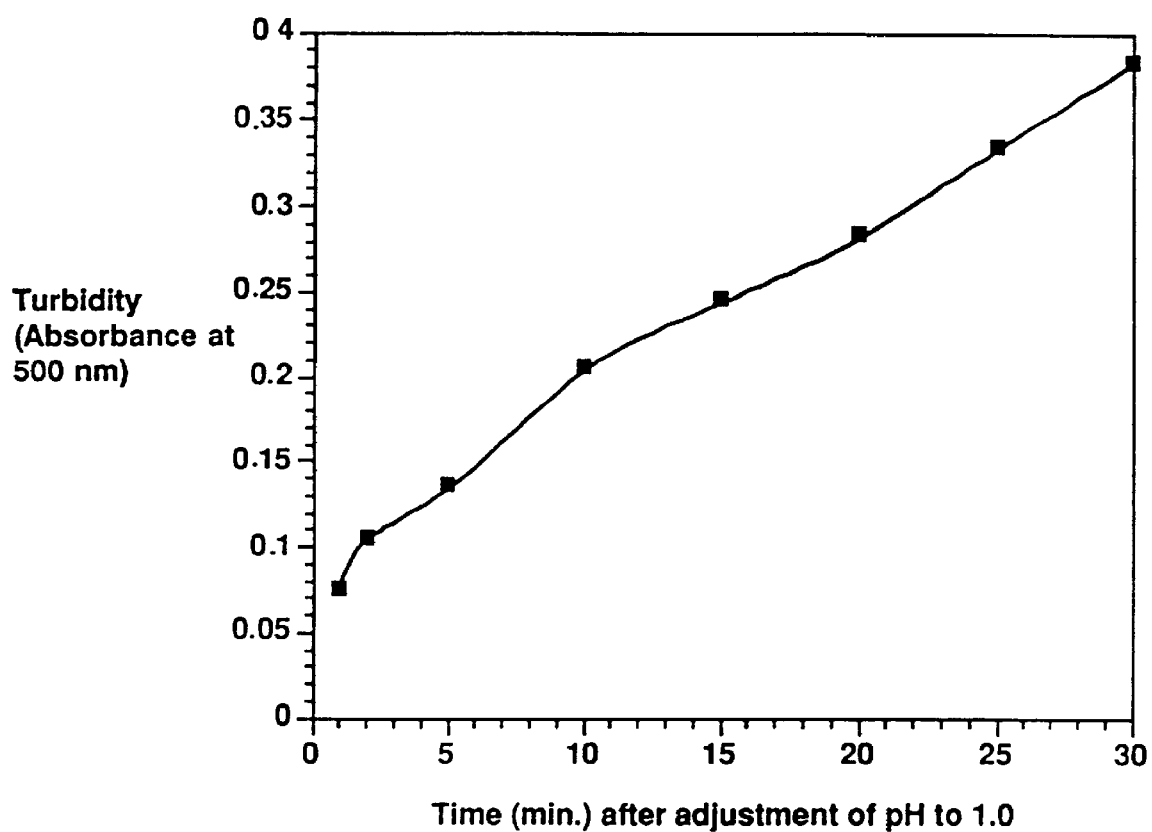
Figure 12:
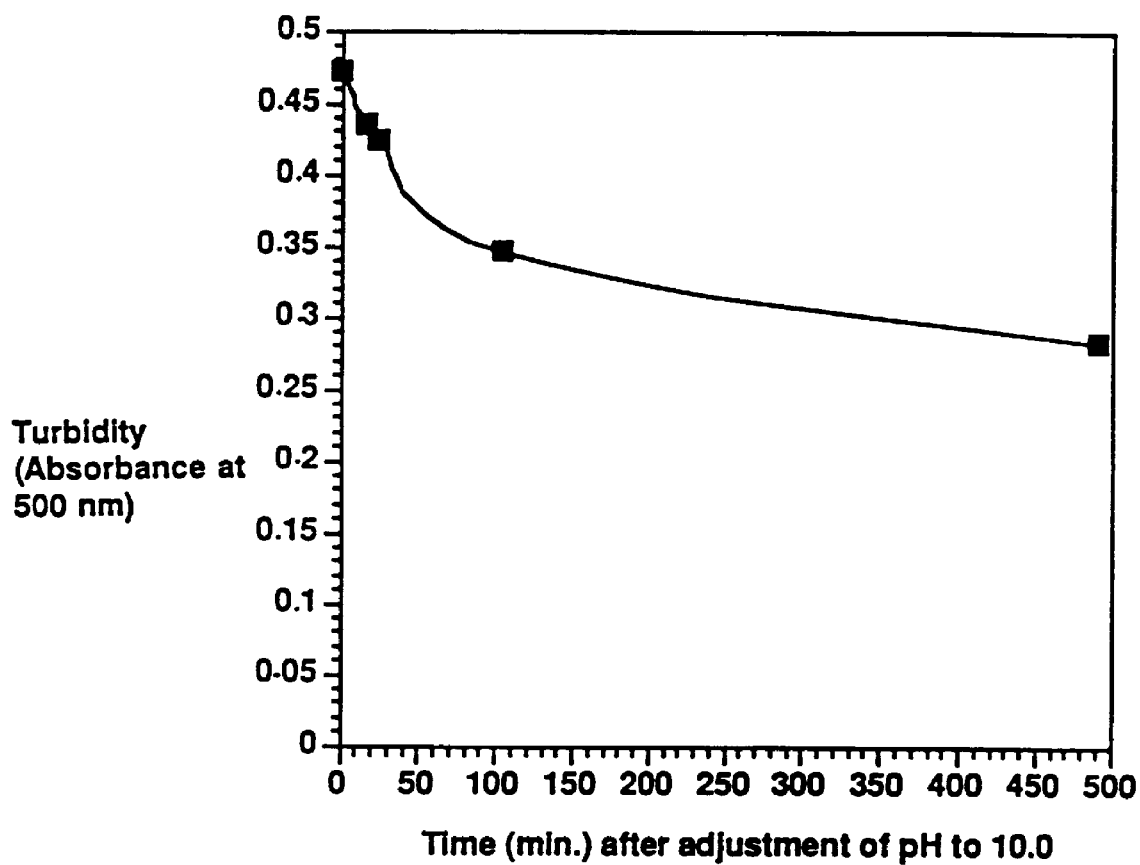

FIGS. 10–12 depict turbidity of a stirred solution of HCA from ascites fluids (Example 12), containing about 100 U/ml of HCA (equivalent in immunoreactivity to 100 ng/ml epiglycanin). The solution pH was adjusted by dropwise addition of phosphoric acid. In FIG. 10., one minute after each addition, the absorbance was read at 500 nm. HCA precipitated spontaneously around pH 1.1. In FIG. 11, the solution was adjusted to pH 1.0 by addition of phosphoric acid, and measurements were taken over the period 5–30 min after that adjustment. NaOH was added to adjust to pH 10.0 with stirring. Aliquots were withdrawn and absorbance was measured (FIG. 12).

EXAMPLE 17
Epiglycanin A

A preferred competitor for competitive HCA immunoassays is an epiglycanin fraction termed Epiglycanin A which is obtained by affinity chromatography (using immobilized peanut lectin) of ascites fluids of mice bearing the TA3-MM/1 ascites cell. The fraction bound to the lectin is termed Epiglycanin B, and the fraction passing through the column freely is Epiglycanin A.

EXAMPLE 18
Competitive Binding Immunoassay

A competitive binding assay (CBA) particularly useful for serum samples was developed for the determination of the concentration of the HCA in human serum. The following steps are employed:

1. Coating. 100 μl of a solution of 25 ng/ml of Epiglycanin-A in phosphate buffered saline (PBS) at pH 7.6 and at 40° C. is incubated in wells for 8–16 hours.

2. Wells are washed after each incubation with PBS.

3. Blocking. A solution of human serum albumin (HSA) (0.6%) in PBS is incubated in the wells for 2 hours.

4. Serum is pre-treated (incubated) with a stabilizing solution (0.010M sodium borate) using a 1:5 sample dilution, at 4° C., for 4–12 hours. This solution is then diluted 1:5 with 0.1% HSA.

5. Monoclonal antibody is diluted with 0.1% HSA at a dilution of approximately 1:(O.D.$_{280}$×10,000).

6. To the washed (PBS) wells are added, in turn, 50 μl of serum (1:25, see 4. above) and 50 μl of diluted antibody (see 5. above).

7. The plate is covered with a plastic sheet and incubated with gentle shaking at 4° C. for 12–18 hours.

8. After washing the plate with PBS, 100 μl of goat anti-mouse IgM, (μ chain specific), phosphatase labeled (1:4,000–10,000) is added, and the plate is incubated at 4° C. with gentle shaking for 3–4 hours.

9. To the washed wells are added 100 μl of substrate (15 mg of paranitrophenyl phosphate in 12 ml of carbonate-bicarbonate buffer, pH 10.3).

10. Color is allowed to develop at room temperature (20°–22° C.). Color intensity is read at 405 nm in a Dynatech automatic plate reader.

EXAMPLE 19
Buoyant Density of HCA

The buoyant density of the HCA from ascites fluid and the KLE-1 cell line was determined by gradient centrifugation in cesium trifluoroacetate according to methods known in the art. Samples of HCA were centrifuged in 47% cesium trifluoroacetate at 130,000×g for 72 h in a Beckmann T-1250 rotor. Fractions of 1 ml were collected, the density of each sample determined, and aliquots of each sample tested for HCA activity by the enzyme competitive binding assay described above. The results of such a binding assay using HCA from ascites fluid of a patient with ovarian carcinoma and spent medium of the KLE-1 cell line are shown in FIGS. 13 and 14, respectively.

Figure 13:
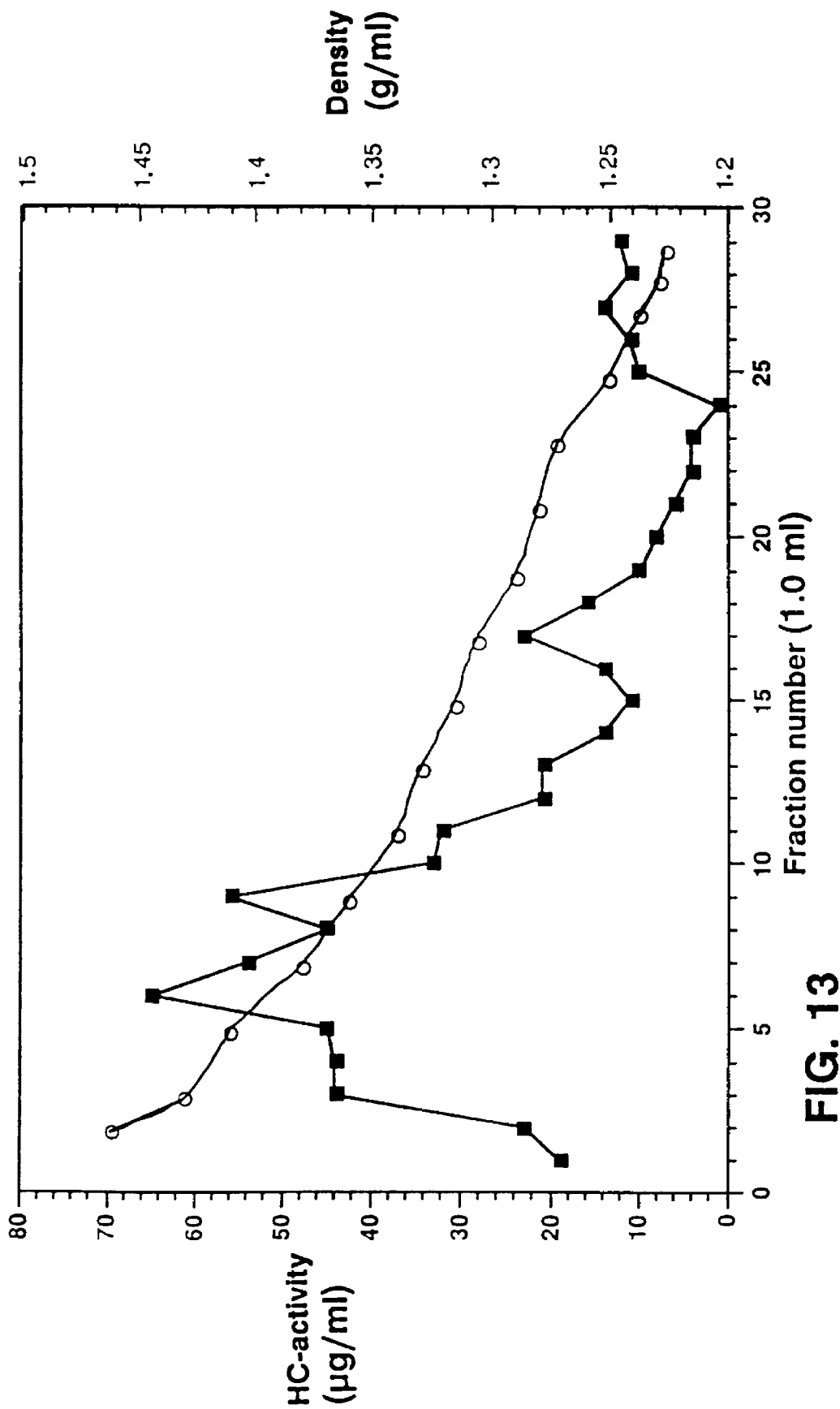
FIGS. 13 and 14 are graphs related to Example 19.

In FIG. 13, HCA purified from human acites fluid (Fraction A from a Sepharose CL-2B column in FIG. 8) was centrifuged at 130,000×g for 72 h in 47% cesium trifluoroacetate (○ represents density). HCA-activity (■) was tested in an enzyme competitive binding assay using anti-EPGN G-1 antibody.

Figure 14:
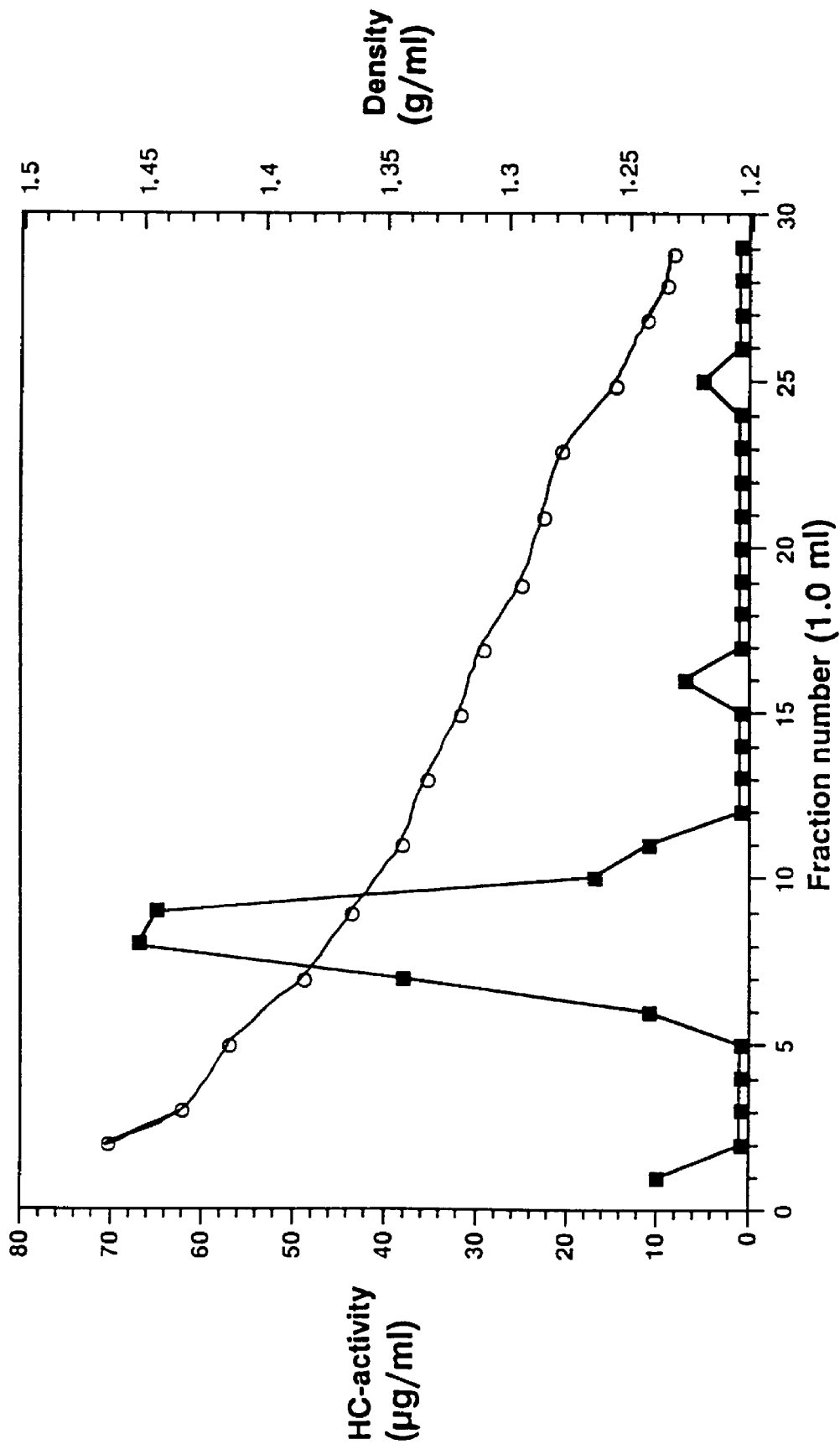

In FIG. 14, HCA purified from spent medium of a cultured endometrial carcinoma cell line (KLE) was centrifuged at 130,000×g for 72 h in 47% cesium trifluoracetate (○ represents density). HCA-activity (■) was tested by an enzyme competitive binding assay using anti-EPGN B-4 antibody.

EXAMPLE 20
Affinity Chromatography using Columns of Immobilized Monoclonal Anti-Epiglycanin Antibodies To purify HCA, samples of spent medium from the KLE-1 cell line or from human ascites fluid were applied to a column (1×5 cm) of Carbolink™ Coupling Gel (Pierce Chemical, Rockford, Ill.) to which anti-epiglycanin AE-3 was covalently coupled. After application of the sample, the column was eluted with PBS pH (7.50), and then with PBS pH (7.50) containing 4M guanidine-HCl. Fractions of 2 ml were collected, aliquots of the fractions diluted, and samples tested for HCA activity by the enzyme competitive binding assay. A typical elution profile for HCA from spent medium of the KLE-1 cell line is shown in FIG. 15.

Figure 15:
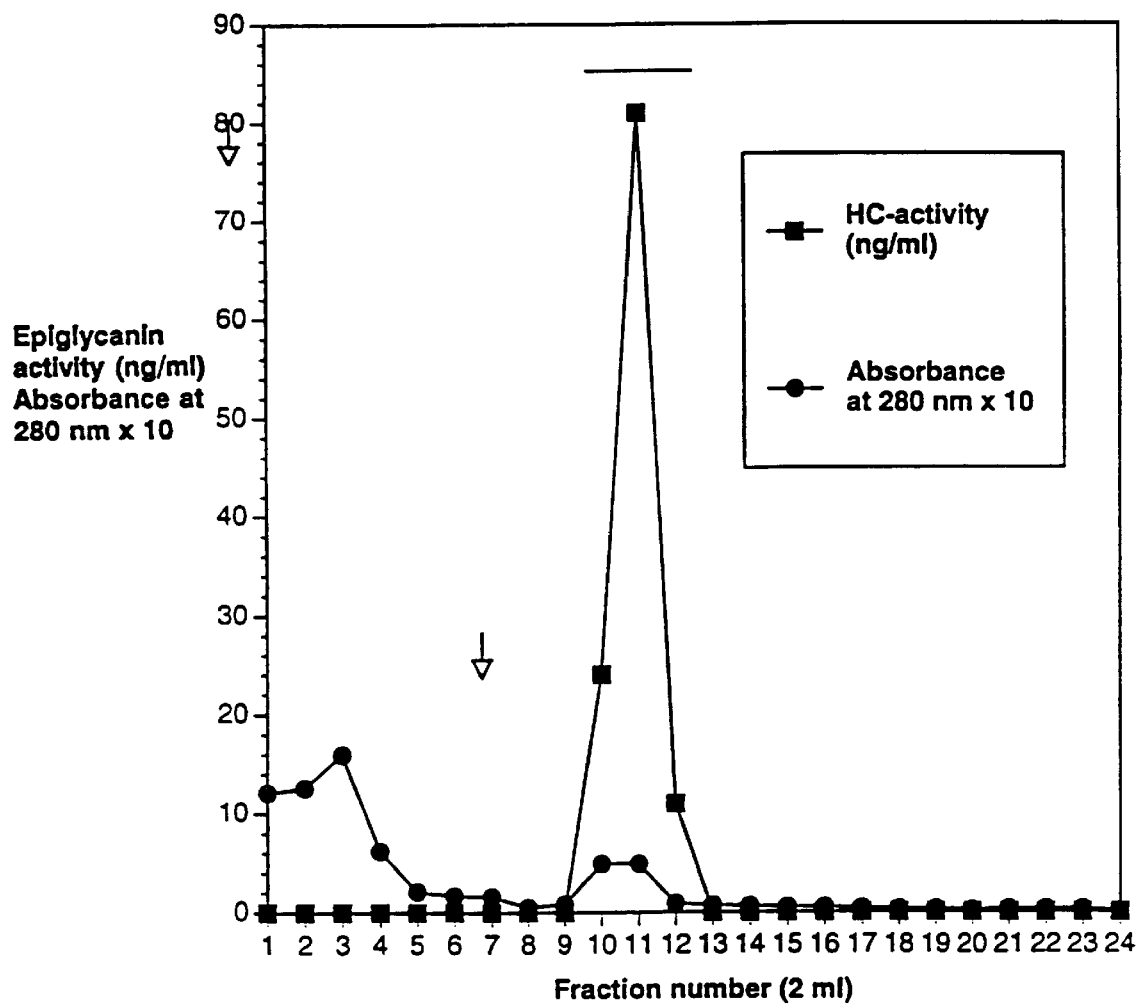
FIG. 15 is a graph related to Example 20.

FIG. 15 shows a chromatographic analysis of spent medium of the human endometrial carcinoma cell line, KLE, on an affinity column of anti-epiglycanin AE-3. Elution with 4M guanidine-HCl was started as indicated by the arrow. The indicated peak fractions were pooled, dialyzed, subjected to SDS-PAGE, and blotted onto PVDF-membrane for further analysis.

EXAMPLE 21
HCA by SDS-PAGE and Visualization of the HCA on Blots

The peak fractions eluted from the affinity column with 4M guanidine-HCl were pooled, dialyzed extensively against distilled water, lyophilized, redissolved in sample buffer for SDS-PAGE containing mercaptoethanol, heated in a boiling water bath for 5 minutes and subjected to SDS-PAGE using an 8% gel (Laemmli, (1970) *Nature* 227:680–685). The electrophoretically separated components were transferred to Immobilon™ PVDF Transfer Membrane (Millipore) by electroblotting. The blots were stained for protein with Coomassie Brilliant Blue R-250 and, HCA was detected by incubation with anti-epiglycanin antibody AE-3, followed by incubation with affinity purified goat-anti mouse IgM conjugated to alkaline phosphatase (Boehringer Mannheim). Visualization of protein bands was accomplished by incubation with a substrate mixture containing naphthol AS-MX phosphate and O-dianisidine, tetrazotized (Fast Blue B-salt) in 0.1M Tris-HCl buffer pH 10.0 and washing with distilled water after appropriate color development (See FIG. 16B).

Figure 16A:
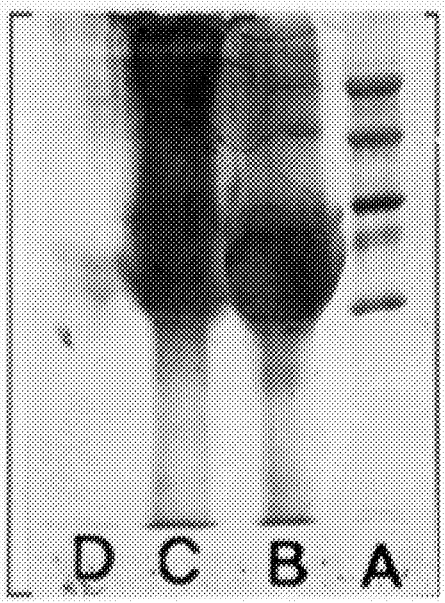
FIGS. 16A and 16B are graphs related to Example 21.
Figure 16B:
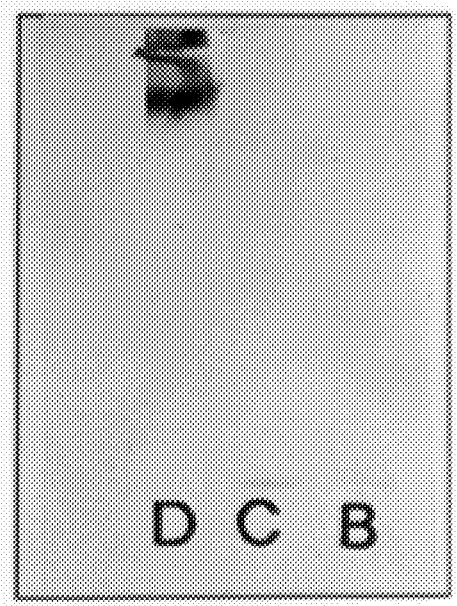

FIGS. 16A and 16B show a Coomassie-stained SDS-PAGE gel 8% polyacrylamide) and a PVDF blot of HCA purified from KLE cells, respectively.

FIG. 16A: (A) Molecular weight standard: myosin (MW 212,000 Da), α-2-macroglobulin (Mw 170,000 Da), β-galactosidase (MW 116,000 Da), transferrin (MW 76,000 Da); (B) Concentrated medium from the KLE cell line applied to affinity column with immobilized AE-3; (C) Material not bound to affinity column with immobilized AE-3; and (D) Fraction bound to AE-3 column and eluted with 4M guanidine-HCl.

FIG. 16B: (B) Concentrated medium from the KLE cell line applied to affinity column with immobilized AE-3; and (C) Material not bound to affinity column with immobilized AE-3; (D) Fraction bound to AE-3 column and eluted with 4M guanidine-HCl.

EXAMPLE 22
Determination of Amino Acid- and Monosaccharide Composition of the HCA After staining with Coomassie Brilliant Blue, the HCA band was excised from the PVDF-membrane. One part of the band was subjected to hydrolysis using 6M HCl in vacuo followed by amino acid analysis of the hydrolysate (Table 1). Another part of the blot was subjected to hydrolysis using 2M trifluoroacetic acid followed by determination of monosaccharide composition by HPAEC-PAD (Weitzhandler, et al. (1993) *J. Biol. Chem.* 268:5121–5130), (Table 2).

TABLE 1

| Amino acid composition of affinity purified HCA from ascites fluid. | |
|---|---|
| Amino Acid | Residues/1000 Residues |
| Serine | 102 |
| Threonine | 36 |
| Glutamine | 146 |
| Asparagine | 82 |
| Leucine | 145 |
| Alanine | 66 |
| Glycine | 234 |
| Valine | 37 |
| Proline | — |
| Lysine | 48 |
| Isoleucine | 37 |
| Arginine | 43 |
| Phenylalanine | traces |
| Tyrosine | traces |
| Histidine | 24 |
| Cysteine | — |

The amino acid composition of the HCA was shown to be significantly different from that of epiglycanin of the mouse mammary carcinoma cell line TA3-Ha (Codington and Haavik (1992) *Glycobiology* 2:173–180), MUC1 (episialin) mouse tumor-associated mucin (Spicer, et al. (1991) *J. Biol. Chem.* 266:15099–15109.), the sialomucin ASGP-1 of the 13762 rat mammary adenocarcinoma cell line (Carraway and Spielman (1986) *Mol. Cell. Biochem.* 72:109–120), TAG-72 from the human colon carcinoma zenograft, LS-174T (Sheer, et al. (1988) *Cancer Res.* 48:6811–6818), epitectin (Ca antigen) isolated from human laryngeal carcinoma (Bhavanandan, et al. (1988) *Ind. J. Biochem. Biophys.* 25:36–42), or pancreatic tumor mucin from the human pancreatic tumor cell line, HPAF (Lan, et al. (1990) *J. Biol. Chem.* 265:15294–15299) (See Table 3).

TABLE 2

| Monosaccharide composition of affinity purified HCA from ascites fluid. | |
|---|---|
| Monosaccharide | Relative Amount |
| Fucose | 1 |
| GalNAc | 4.2 |
| GlcNAc | 3.1 |
| Galactose | 7.7 |
| Mannose | 7.1 |
| NAc neuraminic acid | 4.6 |

Figure 17:
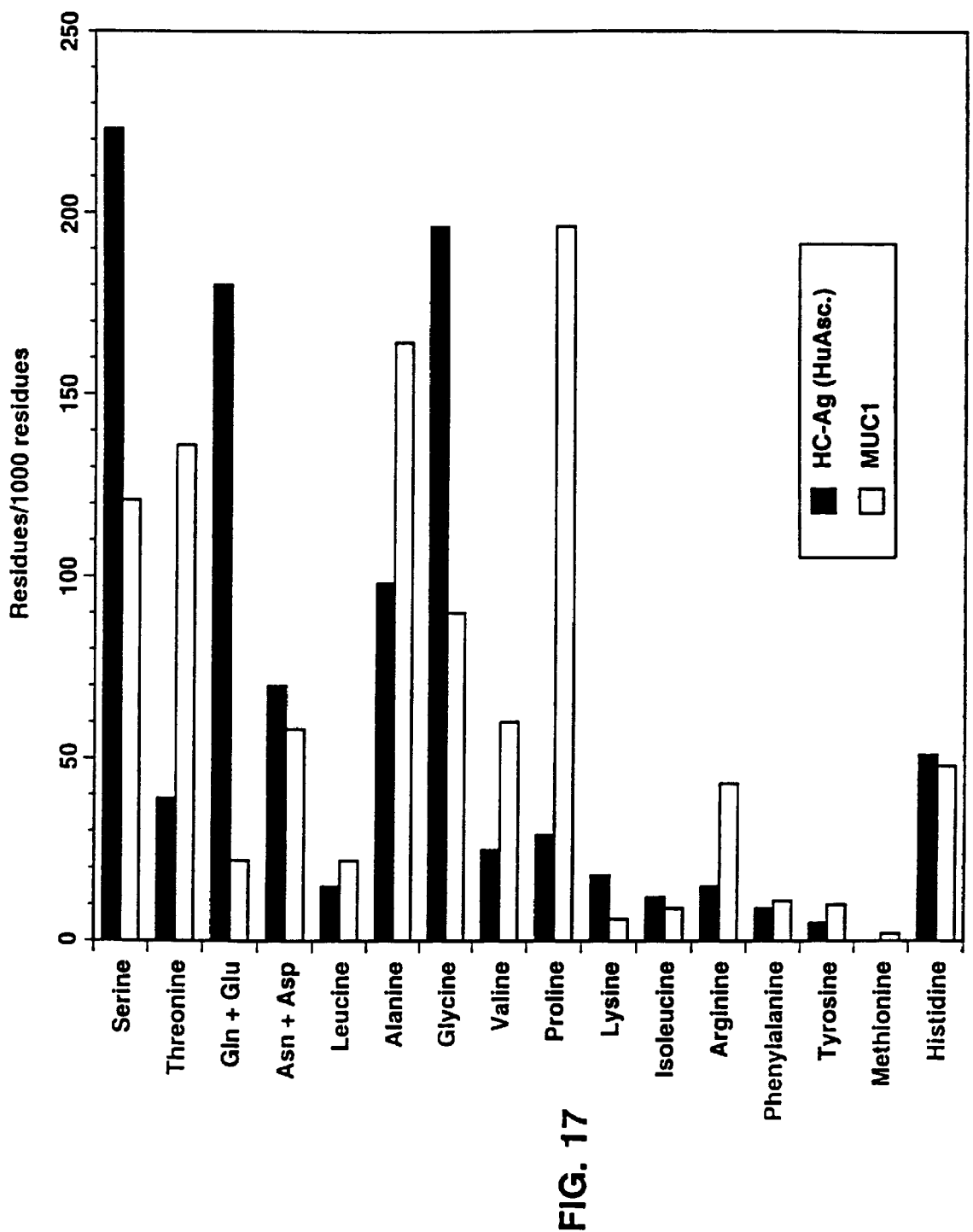
FIGS. 17 and 18 are graphs related to Example 22.
Figure 18:
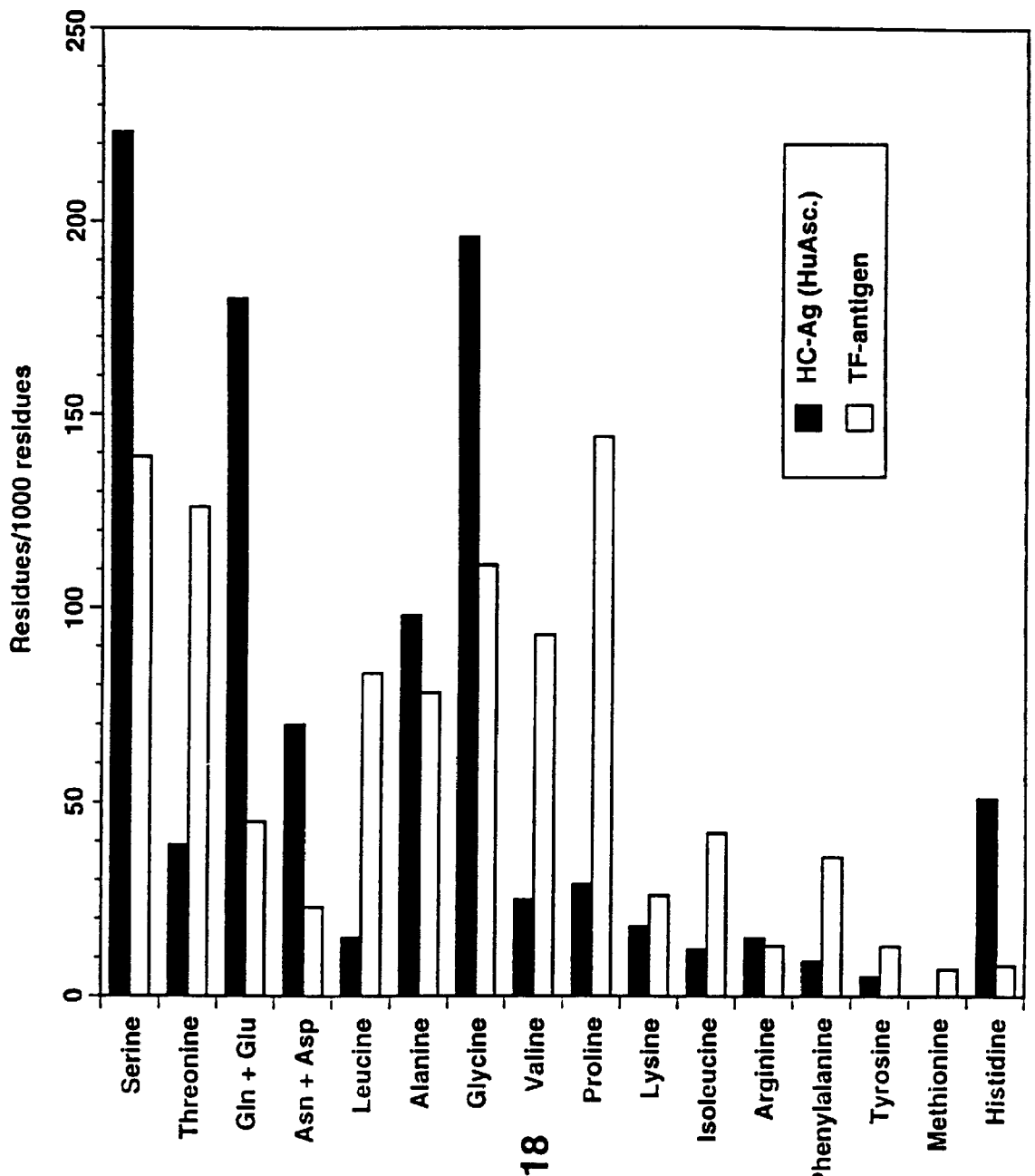

FIG. 17 shows a comparison of the amino acid composition of HCA with MUC1 demonstrating clear differences. Similarly, FIG. 18 shows a comparison of the amino acid composition of HCA with TF antigen (Samuel, et al. U.S. Pat. No. 5,110,911) demonstrating that these antigens vary greatly in their constituent amino acids.

TABLE 3

| Comparison of amino acid compositions of tumor cell sialomucins | | | | | | |
|---|---|---|---|---|---|---|
| Amino acid | EPGN | MUC1 | ASGP | TAG72 | Epit | Hupan | HC-Ag |
| Serine | 230 | 230 | 161 | 177 | 160 | 122 | 102 |
| Threonine | 153 | 126 | 175 | 117 | 69 | 135 | 36 |
| Gln + Glu | 101 | 52 | 134 | 99 | 141 | 10 | 146 |

TABLE 3-continued

Comparison of amino acid compositions of tumor cell sialomucins

| Amino acid | EPGN | MUC1 | ASGP | TAG72 | Epit | Hupan | HC-Ag |
|---|---|---|---|---|---|---|---|
| Asn + Asp | 49 | 74 | 58 | 45 | 91 | 45 | 82 |
| Leucine | 32 | 52 | 60 | 36 | 43 | 27 | 145 |
| Alanine | 101 | 77 | 57 | 54 | 102 | 161 | 66 |
| Glycine | 119 | 54 | 89 | 154 | 175 | 89 | 234 |
| Valine | 39 | 77 | 62 | 38 | 45 | 60 | 37 |
| Proline | 52 | 92 | 72 | 99 | 0 | 190 | 0 |
| Lysine | 27 | 18 | 22 | 37 | 51 | 8 | 48 |
| Isoleucine | 16 | 29 | 23 | 46 | 18 | 9 | 37 |
| Arginine | 29 | 18 | 35 | 78 | 36 | 42 | 43 |
| Phenylala. | 13 | 30 | 16 | 13 | 18 | 10 | 0 |
| Tyrosine | 8 | 29 | 8 | 13 | 18 | 10 | 0 |
| Methionine | 6 | 7 | 7 | 6 | 4 | 3 | 0 |
| Histidine | 26 | 27 | 22 | 32 | 27 | 45 | 24 |

EXAMPLE 23

Specificity study of anti-epiglycanin AE-3

To determine the binding specificity of anti-epiglycanin AE-3, microtiterplate wells coated with epiglycanin were incubated with a mixture of AE-3 antibody and native HCA or HCA that had been incubated with either: 10 mM $NaIO_4$ for 30 min. at 20° C., neuraminidase (*Vibrio cholerae*), endo-α-N-acetylgalactosaminidase (F), Trypsin, or Pronase. The results of these experiments indicated that the antibody AE-3 binds to a carbohydrate-containing epitope or to an epitope that requires a certain carbohydrate structure in order to maintain antibody binding conformation.

Figure 19:
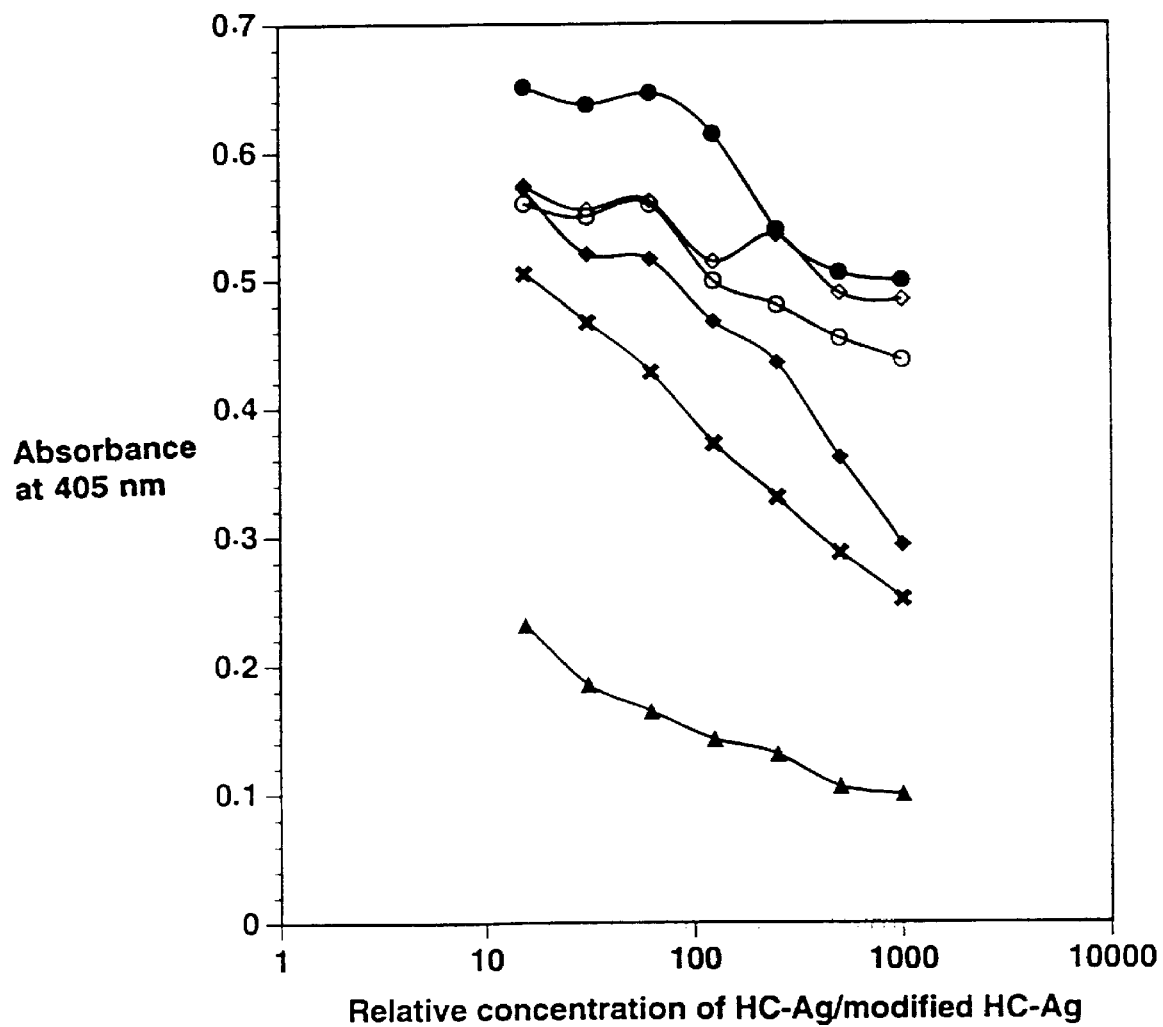
FIG. 19 is a graph related to Example 23.

FIG. 19 shows the competition of binding between epiglycanin and monoclonal anti-epiglycanin antibody AE-3 by HCA or modified HCA isolated from human ascites fluid. Wells coated with epiglycanin were incubated with a mixture of AE-3 antibody and native HCA (×) or HCA that had been incubated with either: 10 mM $NaIO_4$ for 30 min. at 20° (●), neuraminidase (▲), endo-α-N-acetylgalactosaminidase (♦), Trypsin (◊), or Pronase (○).

Treatment of isolated glycoproteins or epiglycanin with TPCK-trypsin, pronase, neuraminidase, O-glycanase or periodate followed by testing of antigenic activity indicated that the anti-epiglycanin antibodies bound to Galβ(1→3) GalNAc-containing epitopes on the glycoproteins.

EXAMPLE 24

Comparison of the specificity of anti-epiglycanin antibodies and other tumor specific antibodies.

Figure 20:
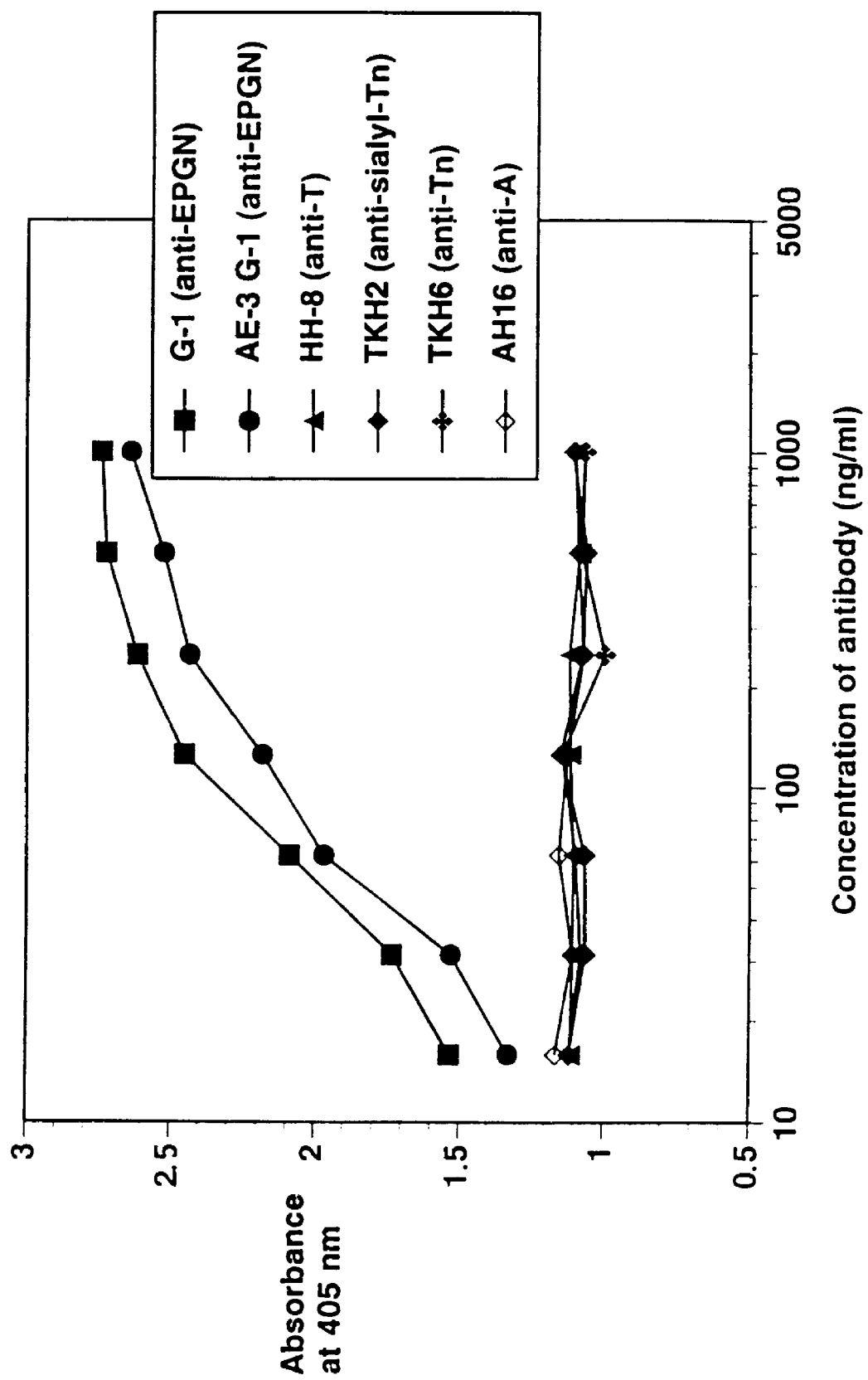
FIGS. 20 and 21 are graphs related to Example 24.

In the experiment shown in FIG. 20, the co-expression and cross-reactivity between the anti-epiglycanin antibodies, G-1 and AE-3, is compared to antibodies against TF-specific antibody, HH8 (Clausen, et al. (1988) *Mol. Immunol.* 25:199–204), sialosyl-Tn-specific antibody, TKH2 (Kjeldsen, et al. (1988) *Cancer Res.* 48:2214–2220), Tn-specific antibody, TKH6 (Clausen and Hakomori (1989) *Vox. Sang.* 56:1–20) and an antibody specific for blood group A antigen, AH16 (Clausen and Hakomori (1989, supra).

A microtiterplate coated with epiglycanin (4–61) was incubated with dilutions of mouse monoclonal antibodies followed by incubation with goat-anti-mouse Ig conjugated with alkaline phosphatase.

FIG. 20 shows that there is negligible cross-reactivity between the anti-epiglycanin antibodies G-1, AE-3 and the antibodies HH8, TKH2, TKH6 or AH16, indicating that the anti-epiglycanin antibodies bind to an altogether different epitope than HH8, TKH2, TKH6, and AH16.

Figure 21:
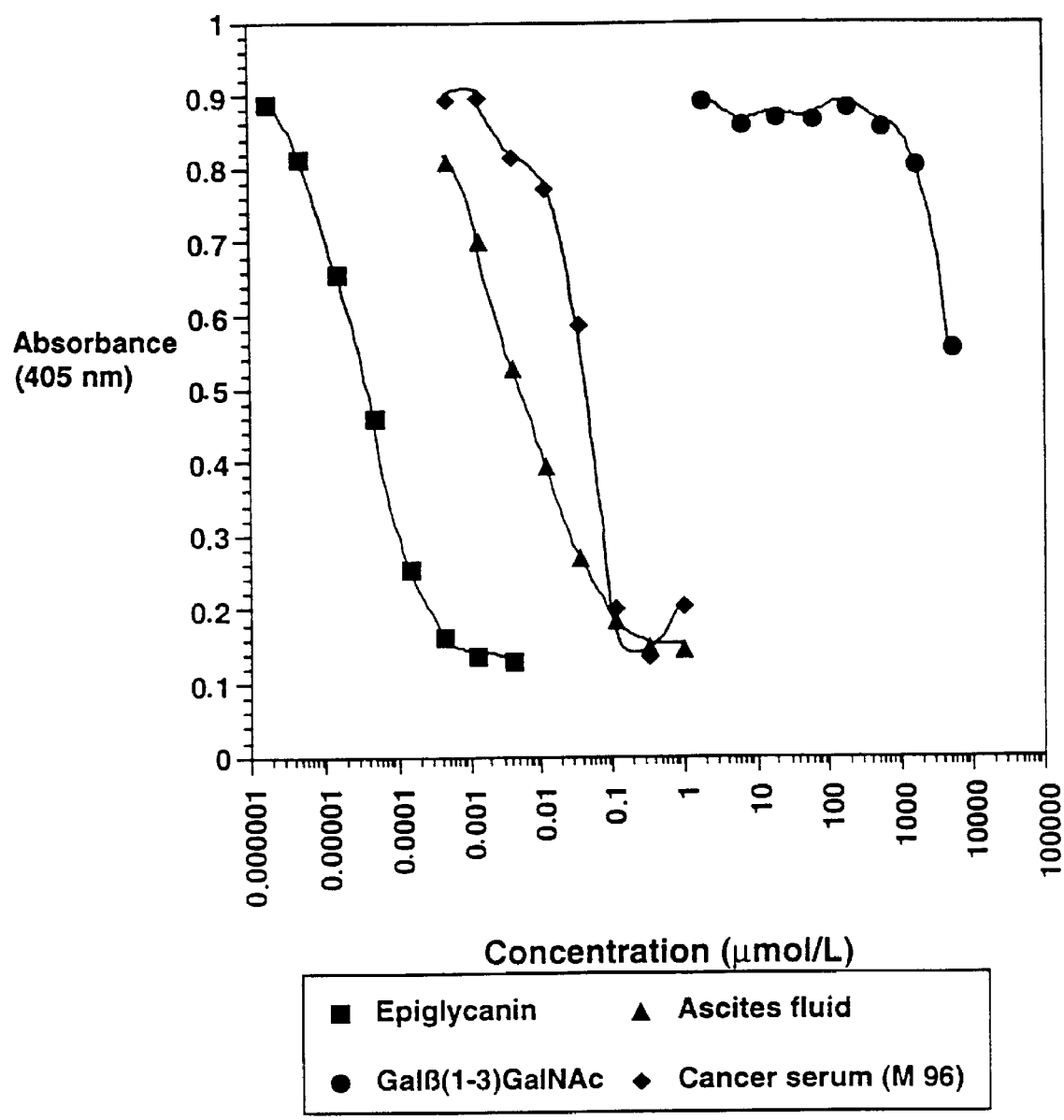

In the experiment shown in FIG. 21, the inhibitory activities of epiglycanin and the disaccharide Galβ (1→3) GalNAc (TF-disaccharide) were compared with respect to ability to inhibit the binding between AE-3 and epiglycanin. A microtiterplate was coated with epiglycanin (4–61), blocked with BSA and incubated with a mixture of anti-epiglycanin AE-3 and inhibitor. The plate was then incubated with goat anti-mouse IgM-alkaline phosphatase. The TF-disaccharide was observed to inhibit the binding between epiglycanin and AE-3 at very high concentrations. However, the inhibitory activity of epiglycanin was about 100 million times higher than that of the TF-disaccharide indicating that epiglycanin and TF-disaccharide are not cross-inhibitory.

EXAMPLE 25

Diagnosis of human carcinoma

Using the immunoassays of the invention, it is possible to detect carcinomas and determine the stage of disease. Using an anti-epiglycanin monoclonal antibody in the competitive binding assay described above, HCA can be identified in the sera of advanced cancer patients.

The competitive binding immunoassay of the invention was carried out using the HCA-specific monoclonal antibody, AE3. In a study performed with sera from 23 Stage four carcinoma patients and 70 normal patients, the levels of HCA in the sera from the Stage four patients were elevated relative to the levels in normal sera. The sensitivity [proportion of Stage four patients with an abnormal (elevated) test values] was found to be 88% when the specificity (proportion of normal patients with normal test values) was held at 95%, demonstrating that the AE3-based immunoassay of the invention differentiates between patients with metastatic cancer and those without disease.

The inter-assay coefficient of variation (standard deviation divided by the mean) was computed using the 70 normals. The coefficient of variation was computed across days within subjects to estimate assay reproducibility. Including all normals, the co-efficient of patient variability was 4.0%. The coefficient of variation was then calculated across subjects to estimate subject variations; this co-efficient of variability was 0.6%. These values are indicative of an assay with a high level of reproducibility.

Other embodiments are within the following claims.

What is claimed is:

1. Human carcinoma antigen (HCA) and immunodeterminant-containing fragments thereof substantially separated from elements of HCA's naturally occurring environment, said HCA being characterized by:
   (a) a molecular weight in excess of 750,000;
   (b) carbohydrate moieties characteristic of mucin-type glycoproteins and the total weight of sialic acid, galactose, N-acetylgalactosamine residues is relatively high in proportion to the total carbohydrate weight;
   (c) an isoelectric point below pH 3.0;
   (d) general presence on human carcinoma cells;
   (e) general absence from non-transformed human cells;
   (f) at least one immunodeterminant that specifically reacts with the anti-murine epiglycanin monoclonal antibody AE3; and
   (g) general insolubility in aqueous fluids below pH 2.0.

2. The HCA of claim 1 and immunodeterminant containing fragments thereof wherein said HCA is characterized by a molecular weight over 1 million.

3. The HCA of claim 1 and immunodeterminant containing fragments thereof wherein the carbohydrate content of said HCA is at least 50% (by weight) made up of the sum of the weights of the sialic acid, galactose, N-acetylgalactosamine, N-acetylglucosamine, mannose and fucose residues.

4. The HCA of claim 1 and immunodeterminant containing fragments thereof wherein said HCA has greater avidity for anti-HCA antibodies than for anti-mouse epiglycanin antibodies.

5. The HCA of claim 1 and immunodeterminant containing fragments thereof wherein said HCA is at least 50% carbohydrate by weight.

6. The HCA of claim 1 and immunodeterminant containing fragments thereof, wherein said HCA comprises the monosaccharide composition of

| Monosaccharide | Amount (±40%) |
|---|---|
| fucose | 3.6% |
| N-acetylgalactosamine | 15.2% |
| N-acetylglucosamine | 11.2% |
| galactose | 27.8% |
| mannose | 25.6% |
| N-acetyl neuraminic acid | 16.6% | as determined by hydrolysis of said HCA using trifluoroacetic acid, followed by determination of monosaccharide composition by high performance anion exchange chromatography with pulsed amperometric detection (HPAEC-PAD).

7. The HCA of claim 1 and immunodeterminant containing fragments thereof, wherein said HCA comprises the monosaccharide composition of

| Monosaccharide | Amount (±10%) |
|---|---|
| fucose | 3.6% |
| N-acetylgalactosamine | 15.2% |
| N-acetylglucosamine | 11.2% |
| galactose | 27.8% |
| mannose | 25.6% |
| N-acetyl neuraminic acid | 16.6% | as determined by hydrolysis of said HCA using trifluoroacetic acid, followed by determination of monosaccharide composition by HPAEC-PAD.

8. The HCA of claim 1 and immunodeterminant containing fragments thereof, wherein said HCA comprises each of the following amino acid residues: Serine, Threonine, Glutamine, Asparagine, Leucine, Alanine, Glycine, Valine, Proline, Lysine, Isoleucine, Arginine, Phenylalanine, Tyrosine, Histidine, Cysteine, and wherein 0–5% of the total amino acid residues in said HCA is Phenylalanine, Tyrosine or Cysteine.

9. The HCA of claim 1 and immunodeterminant containing fragments thereof, wherein said HCA comprises the amino acid composition of

| Amino Acid | Amount (±20%) |
|---|---|
| Serine | 10.2% |
| Threonine | 3.6% |
| Glutamine | 14.6% |
| Asparagine | 8.2% |
| Leucine | 14.5% |
| Alanine | 6.6% |
| Glycine | 23.4% |
| Valine | 3.7% |
| Proline | <1.0% |
| Lysine | 4.8% |
| Isoleucine | 3.7% |
| Arginine | 4.3% |
| Phenylalanine | <1.0% |
| Tyrosine | <1.0% |
| Histidine | 2.4% |
| Cysteine | <1.0% | as determined by hydrolysis of HCA using 6M HCl in vacuo, followed by amino acid analysis.

10. The HCA of claim 1 and immunodeterminant containing fragments thereof, wherein said HCA has a buoyant density of 1.3–1.45 g/ml, as determined by centrifugation in 47% cesium trifluoroacetate.

11. A composition comprising the HCA according to claim 1 or an immunodeterminant containing fragment thereof in a formulation suitable for administration to a human.

12. The composition of claim 11 wherein said composition is a protective vaccine.

13. The composition of claim 11 wherein said composition is an immunotherapeutic suitable for administration to a patient diagnosed with a carcinoma.

* * * * *